US009712385B2

(12) United States Patent
Taylor et al.

(10) Patent No.: US 9,712,385 B2
(45) Date of Patent: *Jul. 18, 2017

(54) MANAGING CONFIGURATIONS OF DISTRIBUTED DEVICES

(71) Applicant: PTC Inc., Needham, MA (US)

(72) Inventors: John Louis Taylor, Webster, NY (US); Timothy A. Rochte, Menlo Park, CA (US); Kiran Bhageshpur, Seattle, WA (US); David Patrick Hart, Webster, NY (US)

(73) Assignee: PTC, Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/091,808

(22) Filed: Apr. 6, 2016

(65) Prior Publication Data

US 2016/0300029 A1 Oct. 13, 2016

Related U.S. Application Data

(63) Continuation of application No. 14/335,428, filed on Jul. 18, 2014, which is a continuation of application
(Continued)

(51) Int. Cl.
*G06F 15/16* (2006.01)
*H04L 12/24* (2006.01)
(Continued)

(52) U.S. Cl.
CPC ........ *H04L 41/0803* (2013.01); *G06F 9/4411* (2013.01); *G06F 19/3412* (2013.01);
(Continued)

(58) Field of Classification Search
CPC .... H04L 41/0803; H04L 67/125; H04L 67/34
See application file for complete search history.

(56) References Cited

U.S. PATENT DOCUMENTS 4,086,434 A 4/1978 Bocchi
4,412,292 A 10/1983 Sedam et al.
(Continued)

FOREIGN PATENT DOCUMENTS

EP 0874306 10/1998
EP 1 191 744 3/2002
(Continued)

OTHER PUBLICATIONS

"Frequently Asked Questions about the Extensible Markup Language—The XML FAQ" Version 1.41 (http://www.oasis-open.org/cover/xmlFAQ141-19981006.html) (Oct. 6, 1998).
(Continued)

*Primary Examiner* — Moustafa M Meky
(74) *Attorney, Agent, or Firm* — Choate, Hall & Stewart LLP; Paul Pysher

(57) ABSTRACT

A method manages configurations of devices in a system that communicates information between a device and an enterprise. The method includes building a defined configuration for a device type. The defined configuration includes a set of value requirements. An actual configuration having values associated with the device is compared to the defined configurations. The actual configuration and defined configuration are stored in a database of the enterprise. The method also includes determining, in the enterprise, if the values of actual configuration match the corresponding value requirements of the defined configurations. The method runs business logic associated with the device based on a result from the step of determining if the values of the actual configuration match the corresponding values of the defined configurations. The matched configurations are stored for subsequent use.

46 Claims, 3 Drawing Sheets

Related U.S. Application Data

No. 13/252,357, filed on Oct. 4, 2011, now Pat. No. 8,788,632, which is a continuation of application No. 11/616,136, filed on Dec. 26, 2006, now Pat. No. 8,065,397.

(51) Int. Cl.
*G06F 9/44* (2006.01)
*G06F 19/00* (2011.01)
*H04L 29/08* (2006.01)

(52) U.S. Cl.
CPC .......... *H04L 67/125* (2013.01); *H04L 67/303* (2013.01); *H04L 67/34* (2013.01)

(56) References Cited

U.S. PATENT DOCUMENTS

| | | |
|---|---|---|
| 4,497,037 A | 1/1985 | Kato et al. |
| 4,583,834 A | 4/1986 | Seko et al. |
| 4,853,946 A | 8/1989 | Elliott et al. |
| 4,962,368 A | 10/1990 | Dobrzanski et al. |
| 4,964,065 A | 10/1990 | Hicks et al. |
| 4,965,946 A | 10/1990 | Hegedus et al. |
| 4,996,703 A | 2/1991 | Gray |
| 5,038,319 A | 8/1991 | Carter et al. |
| 5,057,866 A | 10/1991 | Hill, Jr. et al. |
| 5,061,837 A | 10/1991 | Gilbert et al. |
| 5,062,147 A | 10/1991 | Pickett |
| 5,077,582 A | 12/1991 | Kravette et al. |
| 5,084,875 A | 1/1992 | Weinberger et al. |
| 5,129,080 A | 7/1992 | Smith |
| 5,138,377 A | 8/1992 | Smith et al. |
| 5,163,151 A | 11/1992 | Bronikowski et al. |
| 5,184,179 A | 2/1993 | Tarr et al. |
| 5,204,699 A | 4/1993 | Birnbaum et al. |
| 5,212,645 A | 5/1993 | Wildes et al. |
| 5,214,772 A | 5/1993 | Weinberger et al. |
| 5,216,461 A | 6/1993 | Maekawa et al. |
| 5,220,380 A | 6/1993 | Hirata et al. |
| 5,224,157 A | 6/1993 | Yamada et al. |
| 5,243,382 A | 9/1993 | Takano et al. |
| 5,257,069 A | 10/1993 | Hirata et al. |
| 5,261,061 A | 11/1993 | Ju |
| 5,270,775 A | 12/1993 | Suzuki |
| 5,282,127 A | 1/1994 | Mii |
| 5,291,244 A | 3/1994 | Kajiwara et al. |
| 5,293,196 A | 3/1994 | Kaneko et al. |
| 5,297,034 A | 3/1994 | Weinstein |
| 5,297,256 A | 3/1994 | Wolstenholme et al. |
| 5,300,980 A | 4/1994 | Maekawa et al. |
| 5,303,005 A | 4/1994 | Takano et al. |
| 5,305,055 A | 4/1994 | Ebner et al. |
| 5,305,199 A | 4/1994 | LoBiondo et al. |
| 5,307,263 A | 4/1994 | Brown |
| 5,315,580 A | 5/1994 | Phaal |
| 5,325,156 A | 6/1994 | Ulinski |
| 5,333,286 A | 7/1994 | Weinberger et al. |
| 5,335,048 A | 8/1994 | Takano et al. |
| 5,339,168 A | 8/1994 | Evanitsky et al. |
| 5,342,037 A | 8/1994 | Martin |
| 5,347,346 A | 9/1994 | Shimizu et al. |
| 5,359,391 A | 10/1994 | Kuroyanagi et al. |
| 5,361,265 A | 11/1994 | Weinberger et al. |
| 5,365,310 A | 11/1994 | Jenkins et al. |
| 5,367,667 A | 11/1994 | Wahlquist et al. |
| 5,369,469 A | 11/1994 | Leo et al. |
| 5,369,471 A | 11/1994 | Yamada |
| 5,369,472 A | 11/1994 | Raj et al. |
| 5,373,349 A | 12/1994 | Ito |
| 5,384,622 A | 1/1995 | Hirata et al. |
| 5,386,271 A | 1/1995 | Maekawa et al. |
| 5,392,095 A | 2/1995 | Siegel |
| 5,398,257 A | 3/1995 | Groenteman |
| 5,404,199 A | 4/1995 | Hirata et al. |
| 5,412,779 A | 5/1995 | Motoyama |
| 5,414,494 A | 5/1995 | Aikens et al. |
| 5,420,667 A | 5/1995 | Kaneko et al. |
| 5,420,978 A | 5/1995 | Tozawa et al. |
| 5,424,808 A | 6/1995 | Maekawa et al. |
| 5,424,844 A | 6/1995 | Koyanagi et al. |
| 5,428,551 A | 6/1995 | Trainor et al. |
| 5,430,709 A | 7/1995 | Galloway |
| 5,434,650 A | 7/1995 | Nakahara et al. |
| 5,442,541 A | 8/1995 | Hube et al. |
| 5,444,517 A | 8/1995 | Nagashima |
| 5,444,851 A | 8/1995 | Woest |
| 5,446,522 A | 8/1995 | Tahara et al. |
| 5,452,057 A | 9/1995 | Imaizumi et al. |
| 5,459,552 A | 10/1995 | Ohira |
| 5,463,775 A | 10/1995 | DeWitt et al. |
| 5,469,353 A | 11/1995 | Pinsky et al. |
| 5,485,142 A | 1/1996 | Stute et al. |
| 5,488,454 A | 1/1996 | Fukada et al. |
| 5,491,535 A | 2/1996 | Hirata et al. |
| 5,493,364 A | 2/1996 | Kuroyanagi et al. |
| 5,517,491 A | 5/1996 | Nanni et al. |
| 5,528,691 A | 6/1996 | Rosauer et al. |
| 5,530,899 A | 6/1996 | MacDonald |
| 5,543,892 A | 8/1996 | Hirata et al. |
| 5,548,376 A | 8/1996 | Kikuno |
| 5,550,957 A | 8/1996 | Davidson, Jr. et al. |
| 5,555,191 A | 9/1996 | Hripcsak |
| 5,561,501 A | 10/1996 | Honma |
| 5,572,672 A | 11/1996 | Dewitt et al. |
| 5,579,087 A | 11/1996 | Salgado |
| 5,586,254 A | 12/1996 | Kondo et al. |
| 5,594,529 A | 1/1997 | Yamashita et al. |
| 5,600,301 A | 2/1997 | Robinson, III |
| 5,600,403 A | 2/1997 | Inoo |
| 5,603,060 A | 2/1997 | Weinberger et al. |
| 5,603,323 A | 2/1997 | Pflugrath et al. |
| 5,619,024 A | 4/1997 | Kolls |
| 5,619,716 A | 4/1997 | Nonaka et al. |
| 5,631,724 A | 5/1997 | Sawada et al. |
| 5,636,008 A | 6/1997 | LoBiondo et al. |
| 5,636,333 A | 6/1997 | Davidson, Jr. et al. |
| 5,638,427 A | 6/1997 | Flemming et al. |
| 5,640,495 A | 6/1997 | Colbert et al. |
| 5,642,202 A | 6/1997 | Williams et al. |
| 5,642,208 A | 6/1997 | Takahashi et al. |
| 5,655,084 A | 8/1997 | Pinsky et al. |
| 5,659,794 A | 8/1997 | Caldarale et al. |
| 5,673,190 A | 9/1997 | Kahleck et al. |
| 5,675,744 A | 10/1997 | Tsujii |
| 5,677,775 A | 10/1997 | Yamaguchi et al. |
| 5,694,528 A | 12/1997 | Hube |
| 5,696,903 A | 12/1997 | Mahany |
| 5,699,494 A | 12/1997 | Colbert et al. |
| 5,708,908 A | 1/1998 | Hirata et al. |
| 5,708,909 A | 1/1998 | Yamashita et al. |
| 5,715,393 A | 2/1998 | Naugle |
| 5,715,496 A | 2/1998 | Sawada et al. |
| 5,715,823 A | 2/1998 | Wood et al. |
| 5,720,015 A | 2/1998 | Martin et al. |
| 5,727,135 A | 3/1998 | Webb et al. |
| 5,727,248 A | 3/1998 | Ogura |
| 5,732,212 A | 3/1998 | Perholz et al. |
| 5,736,965 A | 4/1998 | Mosebrook et al. |
| 5,740,801 A | 4/1998 | Branson |
| 5,745,268 A | 4/1998 | Eastvold et al. |
| 5,745,718 A | 4/1998 | Cline et al. |
| 5,748,892 A | 5/1998 | Richardson |
| 5,748,907 A | 5/1998 | Crane |
| 5,752,125 A | 5/1998 | Yamashita et al. |
| 5,752,128 A | 5/1998 | Yamashita |
| 5,752,917 A | 5/1998 | Fuchs |
| 5,761,529 A | 6/1998 | Raji et al. |
| 5,764,918 A | 6/1998 | Poulter |
| 5,768,516 A | 6/1998 | Sugishima |
| 5,772,585 A | 6/1998 | Lavin et al. |
| 5,774,052 A | 6/1998 | Hamm et al. |
| 5,786,994 A | 7/1998 | Friz et al. |
| 5,787,149 A | 7/1998 | Yousefi et al. |
| 5,787,278 A | 7/1998 | Barton et al. |

(56) References Cited

U.S. PATENT DOCUMENTS

| | | |
|---|---|---|
| 5,790,793 A | 8/1998 | Higley |
| 5,790,977 A | 8/1998 | Exekiel |
| 5,798,738 A | 8/1998 | Yamada |
| 5,801,964 A | 9/1998 | McCarthy |
| 5,809,237 A | 9/1998 | Watts et al. |
| 5,809,297 A | 9/1998 | Kroenke et al. |
| 5,812,397 A | 9/1998 | Pech et al. |
| 5,812,874 A | 9/1998 | Yamashita et al. |
| 5,818,603 A | 10/1998 | Motoyama |
| 5,819,015 A | 10/1998 | Martin et al. |
| 5,819,110 A | 10/1998 | Motoyama |
| 5,822,221 A | 10/1998 | Groenteman |
| 5,826,027 A | 10/1998 | Pedersen et al. |
| 5,828,943 A | 10/1998 | Brown |
| 5,835,816 A | 11/1998 | Sawada et al. |
| 5,835,911 A | 11/1998 | Nakagawa et al. |
| 5,844,550 A | 12/1998 | Trainor et al. |
| 5,845,061 A | 12/1998 | Miyamoto et al. |
| 5,845,230 A | 12/1998 | Lamberson |
| 5,857,207 A | 1/1999 | Lo et al. |
| 5,857,967 A | 1/1999 | Frid et al. |
| 5,862,348 A | 1/1999 | Pedersen |
| 5,862,404 A | 1/1999 | Onaga |
| 5,865,745 A | 2/1999 | Schmitt et al. |
| 5,872,635 A | 2/1999 | Akiyama |
| 5,872,928 A | 2/1999 | Lewis et al. |
| 5,873,009 A | 2/1999 | Yamashita et al. |
| 5,873,659 A | 2/1999 | Edwards et al. |
| 5,878,746 A | 3/1999 | Lemelson et al. |
| 5,880,677 A | 3/1999 | Lestician |
| 5,884,072 A | 3/1999 | Rasmussen |
| 5,887,216 A | 3/1999 | Motoyama |
| 5,890,029 A | 3/1999 | Hirata et al. |
| 5,894,416 A | 4/1999 | Kuroyanagi et al. |
| 5,897,235 A | 4/1999 | Honma |
| 5,901,286 A | 5/1999 | Danknick et al. |
| 5,905,906 A | 5/1999 | Goffinet et al. |
| 5,909,493 A | 6/1999 | Motoyama et al. |
| 5,911,095 A | 6/1999 | Atsumi et al. |
| 5,913,060 A | 6/1999 | Discavage |
| 5,917,405 A | 6/1999 | Joao |
| 5,923,842 A | 7/1999 | Pedersen et al. |
| 5,933,675 A | 8/1999 | Sawada et al. |
| 5,935,060 A | 8/1999 | Iliff |
| 5,941,949 A | 8/1999 | Pedersen |
| 5,956,487 A | 9/1999 | Venkatraman et al. |
| 5,956,698 A | 9/1999 | Lachese et al. |
| 5,961,586 A | 10/1999 | Pedersen |
| 5,968,116 A | 10/1999 | Day et al. |
| 5,970,149 A | 10/1999 | Johnson |
| 5,974,234 A | 10/1999 | Levine et al. |
| 5,975,737 A | 11/1999 | Crater et al. |
| 5,991,810 A | 11/1999 | Shapiro et al. |
| 6,003,061 A | 12/1999 | Jones et al. |
| 6,003,070 A | 12/1999 | Frantz |
| 6,003,078 A | 12/1999 | Kodimer et al. |
| 6,006,045 A | 12/1999 | Miyawaki |
| 6,009,274 A | 12/1999 | Fletcher et al. |
| 6,009,284 A | 12/1999 | Weinberger et al. |
| 6,012,088 A | 1/2000 | Li et al. |
| 6,014,631 A | 1/2000 | Teagarden et al. |
| 6,014,691 A | 1/2000 | Brewer et al. |
| 6,014,694 A | 1/2000 | Aharoni et al. |
| 6,016,535 A | 1/2000 | Krantz et al. |
| 6,021,284 A | 2/2000 | Serizawa et al. |
| 6,022,315 A | 2/2000 | Iliff |
| 6,023,223 A | 2/2000 | Baxter, Jr. |
| 6,023,507 A | 2/2000 | Wookey |
| 6,023,721 A | 2/2000 | Cummings |
| 6,023,749 A | 2/2000 | Richardson |
| 6,025,925 A | 2/2000 | Davidson, Jr. et al. |
| 6,031,964 A | 2/2000 | Anderson |
| 6,041,041 A | 3/2000 | Ramanathan et al. |
| 6,042,111 A | 3/2000 | Rivers et al. |
| 6,057,857 A | 5/2000 | Bloomfield |
| 6,060,994 A | 5/2000 | Chen |
| 6,061,603 A | 5/2000 | Papadopolous et al. |
| 6,064,915 A | 5/2000 | Kaneko et al. |
| 6,065,118 A | 5/2000 | Bull et al. |
| 6,081,623 A | 6/2000 | Bloomfield et al. |
| 6,088,718 A | 7/2000 | Altschuler et al. |
| 6,091,915 A | 7/2000 | Takagishi |
| 6,098,116 A | 8/2000 | Nixon et al. |
| 6,101,407 A | 8/2000 | Groezinger |
| 6,108,492 A | 8/2000 | Miyachi |
| 6,112,035 A | 8/2000 | Kuroyanagi et al. |
| 6,112,256 A | 8/2000 | Goffinet et al. |
| 6,115,489 A | 9/2000 | Gupta et al. |
| 6,118,899 A | 9/2000 | Bloomfield et al. |
| 6,119,934 A | 9/2000 | Kolls |
| 6,122,463 A | 9/2000 | Nagatani |
| 6,125,363 A | 9/2000 | Buzzeo et al. |
| 6,130,999 A | 10/2000 | Serizawa et al. |
| 6,139,177 A | 10/2000 | Venkatraman et al. |
| 6,141,737 A | 10/2000 | Krantz et al. |
| 6,152,365 A | 11/2000 | Kolls |
| 6,157,944 A | 12/2000 | Pedersen |
| 6,161,145 A | 12/2000 | Bainbridge |
| 6,163,317 A | 12/2000 | de Judicibus |
| 6,167,432 A | 12/2000 | Jiang |
| 6,167,448 A | 12/2000 | Hemphill et al. |
| 6,172,683 B1 | 1/2001 | Bloomfield |
| 6,175,866 B1 | 1/2001 | Holloway et al. |
| 6,181,331 B1 | 1/2001 | Trainor et al. |
| 6,189,113 B1 | 2/2001 | Rabb et al. |
| 6,196,735 B1 | 3/2001 | Inamine |
| 6,205,466 B1 | 3/2001 | Karp et al. |
| 6,209,048 B1 | 3/2001 | Wolff |
| 6,221,011 B1 | 4/2001 | Bardy |
| 6,226,650 B1 | 5/2001 | Mahajan et al. |
| 6,230,199 B1 | 5/2001 | Revashetti et al. |
| 6,246,485 B1 | 6/2001 | Brown et al. |
| 6,256,378 B1 | 7/2001 | Iggulden et al. |
| 6,256,668 B1 | 7/2001 | Slivka et al. |
| 6,260,148 B1 | 7/2001 | Aggarwal et al. |
| 6,260,248 B1 | 7/2001 | Cramer et al. |
| 6,282,454 B1 | 8/2001 | Papadopolous et al. |
| 6,282,711 B1 | 8/2001 | Halpern et al. |
| 6,286,038 B1 | 9/2001 | Reichmeyer et al. |
| 6,286,059 B1 | 9/2001 | Sugiura |
| 6,289,461 B1 | 9/2001 | Dixon |
| 6,292,828 B1 | 9/2001 | Williams |
| 6,295,527 B1 | 9/2001 | McCormack et al. |
| 6,298,457 B1 | 10/2001 | Rachlin et al. |
| 6,304,895 B1 | 10/2001 | Schneider et al. |
| 6,307,570 B1 | 10/2001 | Stergiades |
| 6,308,099 B1 | 10/2001 | Fox et al. |
| 6,311,024 B1 | 10/2001 | Serizawa et al. |
| 6,312,378 B1 | 11/2001 | Bardy |
| 6,317,570 B1 | 11/2001 | Uchida et al. |
| 6,317,783 B1 | 11/2001 | Freishtat et al. |
| 6,317,848 B1 | 11/2001 | Sorens et al. |
| 6,325,540 B1 | 12/2001 | Lounsberry et al. |
| 6,327,594 B1 | 12/2001 | Van Huben et al. |
| 6,338,086 B1 | 1/2002 | Curtis et al. |
| 6,343,320 B1 | 1/2002 | Fairchild et al. |
| 6,356,933 B2 | 3/2002 | Mitchell et al. |
| 6,356,949 B1 | 3/2002 | Katsandres et al. |
| 6,366,741 B1 | 4/2002 | Fukushima |
| 6,368,284 B1 | 4/2002 | Bardy |
| 6,370,552 B1 | 4/2002 | Bloomfield |
| 6,370,570 B1 | 4/2002 | Muir et al. |
| 6,370,582 B1 | 4/2002 | Lim et al. |
| 6,377,162 B1 | 4/2002 | Delestienne et al. |
| 6,377,971 B1 | 4/2002 | Madden et al. |
| 6,381,557 B1 | 4/2002 | Babula et al. |
| 6,397,212 B1 | 5/2002 | Biffar |
| 6,405,310 B1 | 6/2002 | Simpson |
| 6,406,426 B1 | 6/2002 | Reuss et al. |
| 6,412,026 B1 | 6/2002 | Graf |
| 6,415,023 B2 | 7/2002 | Iggulden |
| 6,415,392 B1 | 7/2002 | Suzuki et al. |
| 6,421,671 B1 | 7/2002 | Bryan et al. |
| 6,426,798 B1 | 7/2002 | Yeung |

(56) References Cited

U.S. PATENT DOCUMENTS

| | | |
|---|---|---|
| 6,430,612 B1 | 8/2002 | Iizuka |
| 6,430,711 B1 | 8/2002 | Sekizawa |
| 6,434,572 B2 | 8/2002 | Derzay et al. |
| 6,437,692 B1 | 8/2002 | Petite et al. |
| 6,437,803 B1 | 8/2002 | Panasyuk et al. |
| 6,438,598 B1 | 8/2002 | Pedersen |
| 6,446,192 B1 | 9/2002 | Narasimhan et al. |
| 6,449,633 B1 | 9/2002 | Van et al. |
| 6,449,663 B1 | 9/2002 | Carney et al. |
| 6,453,127 B2 | 9/2002 | Wood et al. |
| 6,453,129 B1 | 9/2002 | Simpson et al. |
| 6,457,038 B1 | 9/2002 | Defosse |
| 6,462,831 B1 | 10/2002 | Akiyama |
| 6,466,971 B1 | 10/2002 | Humpleman et al. |
| 6,471,521 B1 | 10/2002 | Dornbush et al. |
| 6,477,117 B1 | 11/2002 | Narayanaswami et al. |
| 6,479,792 B1 | 11/2002 | Beiermann et al. |
| 6,487,513 B1 | 11/2002 | Eastvold et al. |
| 6,493,517 B1 | 12/2002 | Hanson |
| 6,493,871 B1 | 12/2002 | McGuire et al. |
| 6,494,831 B1 | 12/2002 | Koritzinsky |
| 6,502,132 B1 | 12/2002 | Kumano |
| 6,510,350 B1 | 1/2003 | Steen et al. |
| 6,510,454 B1 | 1/2003 | Walukiewicz |
| 6,523,013 B2 | 2/2003 | Shah et al. |
| 6,523,063 B1 | 2/2003 | Miller et al. |
| 6,523,130 B1 | 2/2003 | Hickman et al. |
| 6,529,848 B2 | 3/2003 | Sone |
| 6,538,667 B1 | 3/2003 | Duursma et al. |
| 6,549,612 B2 | 4/2003 | Gifford et al. |
| 6,553,336 B1 | 4/2003 | Johnson et al. |
| 6,553,490 B1 | 4/2003 | Kottapurath et al. |
| 6,559,965 B1 | 5/2003 | Simpson et al. |
| 6,560,611 B1 | 5/2003 | Nine et al. |
| 6,560,641 B1 | 5/2003 | Powderly et al. |
| 6,560,656 B1 | 5/2003 | O'Sullivan et al. |
| 6,564,227 B2 | 5/2003 | Sakakibara et al. |
| 6,567,813 B1 | 5/2003 | Zhu et al. |
| 6,574,729 B1 | 6/2003 | Fink et al. |
| 6,581,092 B1 | 6/2003 | Motoyama et al. |
| 6,581,094 B1 | 6/2003 | Gao |
| 6,587,812 B1 | 7/2003 | Takayama |
| 6,591,272 B1 | 7/2003 | Williams |
| 6,598,011 B1 | 7/2003 | Howards Koritzinsky et al. |
| 6,601,087 B1 | 7/2003 | Zhu et al. |
| 6,601,159 B1 | 7/2003 | Smith et al. |
| 6,604,212 B2 | 8/2003 | Sekizawa et al. |
| 6,609,108 B1 | 8/2003 | Pulliam et al. |
| 6,611,863 B1 | 8/2003 | Banginwar |
| 6,631,407 B1 | 10/2003 | Mukaiyama et al. |
| 6,636,899 B1 | 10/2003 | Rabb et al. |
| 6,643,650 B1 | 11/2003 | Slaughter et al. |
| 6,643,690 B2 | 11/2003 | Duursma et al. |
| 6,646,655 B1 | 11/2003 | Brandt et al. |
| 6,651,110 B1 | 11/2003 | Caspers et al. |
| 6,651,190 B1 | 11/2003 | Worley et al. |
| 6,654,032 B1 | 11/2003 | Zhu et al. |
| 6,654,720 B1 | 11/2003 | Graham et al. |
| 6,654,726 B1 | 11/2003 | Hanzek |
| 6,665,425 B1 | 12/2003 | Sampath et al. |
| 6,670,810 B2 | 12/2003 | Duncan et al. |
| 6,671,695 B2 | 12/2003 | McFadden |
| 6,675,197 B1 | 1/2004 | Satoh et al. |
| 6,681,344 B1 | 1/2004 | Andrew |
| 6,681,349 B2 | 1/2004 | Sekizawa |
| 6,684,259 B1 | 1/2004 | Discavage et al. |
| 6,686,838 B1 | 2/2004 | Rezvani et al. |
| 6,687,848 B1 | 2/2004 | Najmi |
| 6,687,873 B1 | 2/2004 | Ballantyne et al. |
| 6,691,106 B1 | 2/2004 | Sathyanarayan |
| 6,691,154 B1 | 2/2004 | Zhu et al. |
| 6,691,157 B2 | 2/2004 | Muir et al. |
| 6,704,807 B1 | 3/2004 | Mathur et al. |
| 6,710,893 B1 | 3/2004 | Hou et al. |
| 6,711,593 B1 | 3/2004 | Gordon et al. |
| 6,711,618 B1 | 3/2004 | Danner et al. |
| 6,717,513 B1 | 4/2004 | Sandelman et al. |
| 6,738,798 B1 | 5/2004 | Ploetz et al. |
| 6,754,664 B1 | 6/2004 | Bush |
| 6,757,714 B1 | 6/2004 | Hansen |
| 6,757,899 B2 | 6/2004 | Zhdankin et al. |
| 6,760,761 B1 | 7/2004 | Sciacca |
| 6,763,274 B1 | 7/2004 | Gilbert |
| 6,763,501 B1 | 7/2004 | Zhu et al. |
| 6,766,333 B1 | 7/2004 | Wu et al. |
| 6,775,238 B1 | 8/2004 | Suzuki et al. |
| 6,779,004 B1 | 8/2004 | Zintel |
| 6,782,542 B1 | 8/2004 | Mein et al. |
| 6,785,015 B1 | 8/2004 | Smith et al. |
| 6,785,713 B1 | 8/2004 | Freeman et al. |
| 6,785,726 B1 | 8/2004 | Freeman et al. |
| 6,789,112 B1 | 9/2004 | Freeman et al. |
| 6,789,119 B1 | 9/2004 | Zhu et al. |
| 6,792,337 B2 | 9/2004 | Blackett et al. |
| 6,799,209 B1 | 9/2004 | Hayton |
| 6,799,270 B1 | 9/2004 | Bull et al. |
| RE38,609 E | 10/2004 | Chen et al. |
| 6,804,712 B1 | 10/2004 | Kracht |
| 6,807,580 B2 | 10/2004 | Freeman et al. |
| 6,810,488 B2 | 10/2004 | Teng |
| 6,816,616 B2 | 11/2004 | Teng |
| 6,823,397 B2 | 11/2004 | Rawson, III |
| 6,826,606 B2 | 11/2004 | Freeman et al. |
| 6,831,555 B1 | 12/2004 | Miller et al. |
| 6,832,239 B1 | 12/2004 | Kraft et al. |
| 6,832,373 B2 | 12/2004 | O'Neill |
| 6,834,298 B1 | 12/2004 | Singer et al. |
| 6,842,903 B1 | 1/2005 | Weschler |
| 6,857,013 B2 | 2/2005 | Ramberg et al. |
| 6,886,046 B2 | 4/2005 | Stutz et al. |
| 6,891,830 B2 | 5/2005 | Curtis |
| 6,901,448 B2 | 5/2005 | Zhu et al. |
| 6,904,593 B1 | 6/2005 | Fong et al. |
| 6,920,480 B2 | 7/2005 | Mitchell et al. |
| 6,922,724 B1 | 7/2005 | Freeman et al. |
| 6,925,335 B2 | 8/2005 | May et al. |
| 6,925,645 B2 | 8/2005 | Zhu et al. |
| 6,928,469 B1 | 8/2005 | Duursma et al. |
| 6,940,405 B2 | 9/2005 | Script et al. |
| 6,950,991 B2 | 9/2005 | Bloomfield et al. |
| 6,952,714 B2 | 10/2005 | Peart |
| 6,963,899 B1 | 11/2005 | Fernandez et al. |
| 6,972,676 B1 | 12/2005 | Kimmel et al. |
| 6,983,020 B2 | 1/2006 | Christiansen |
| 6,985,779 B2 | 1/2006 | Hsiung et al. |
| 6,986,040 B1 | 1/2006 | Kramer et al. |
| 6,990,395 B2 | 1/2006 | Ransom et al. |
| 7,003,574 B1 | 2/2006 | Bahl |
| 7,016,966 B1 | 3/2006 | Saulpaugh et al. |
| 7,020,706 B2 | 3/2006 | Cates et al. |
| 7,020,773 B1 | 3/2006 | Otway et al. |
| 7,028,025 B2 | 4/2006 | Collins |
| 7,028,081 B2 | 4/2006 | Kawashima |
| 7,031,342 B2 | 4/2006 | Teng |
| 7,032,005 B2 | 4/2006 | Mathon et al. |
| 7,043,677 B1 | 5/2006 | Li |
| 7,046,134 B2 | 5/2006 | Hansen |
| 7,051,084 B1 | 5/2006 | Hayton et al. |
| 7,057,724 B1 | 6/2006 | Mead et al. |
| 7,065,576 B2 | 6/2006 | Kamel et al. |
| 7,069,298 B2 | 6/2006 | Zhu et al. |
| 7,072,946 B2 | 7/2006 | Shafer |
| 7,079,010 B2 | 7/2006 | Champlin |
| 7,080,267 B2 | 7/2006 | Gary et al. |
| 7,082,426 B2 | 7/2006 | Musgrove et al. |
| 7,082,460 B2 | 7/2006 | Hansen et al. |
| 7,085,814 B1 | 8/2006 | Gandhi et al. |
| 7,085,824 B2 | 8/2006 | Forth et al. |
| 7,089,567 B2 | 8/2006 | Girardot et al. |
| 7,091,846 B2 | 8/2006 | Wu |
| 7,092,370 B2 | 8/2006 | Jiang et al. |
| 7,099,110 B2 | 8/2006 | Detzler |
| 7,100,200 B2 | 8/2006 | Pope et al. |
| 7,103,357 B2 | 9/2006 | Kirani et al. |

(56) References Cited

U.S. PATENT DOCUMENTS

| | | |
|---|---|---|
| 7,103,799 B2 | 9/2006 | Dixon |
| 7,107,312 B2 | 9/2006 | Hackbarth |
| 7,113,988 B2 | 9/2006 | Chirashya et al. |
| 7,116,681 B1 | 10/2006 | Hovell et al. |
| 7,117,239 B1 | 10/2006 | Hansen |
| 7,117,243 B2 | 10/2006 | Peart |
| 7,127,525 B2 | 10/2006 | Coleman et al. |
| 7,130,883 B2 | 10/2006 | Zhu et al. |
| 7,142,839 B2 | 11/2006 | Pelaez et al. |
| 7,143,153 B1 | 11/2006 | Black |
| 7,149,792 B1 | 12/2006 | Hansen |
| 7,158,483 B1 | 1/2007 | Takabatake et al. |
| 7,162,315 B2 | 1/2007 | Gilbert |
| 7,162,628 B2 | 1/2007 | Gentil et al. |
| 7,178,149 B2 | 2/2007 | Hansen |
| 7,185,014 B1 | 2/2007 | Hansen |
| 7,194,743 B2 | 3/2007 | Hayton et al. |
| 7,203,755 B2 | 4/2007 | Zhu et al. |
| 7,213,051 B2 | 5/2007 | Zhu et al. |
| 7,216,172 B2 | 5/2007 | Yang et al. |
| 7,234,943 B1 | 6/2007 | Aleali |
| 7,254,601 B2 | 8/2007 | Baller et al. |
| 7,266,526 B1 | 9/2007 | Drummond et al. |
| 7,290,061 B2 | 10/2007 | Lentini et al. |
| 7,293,176 B2 | 11/2007 | Otway et al. |
| 7,330,872 B2 | 2/2008 | Peart et al. |
| 7,334,119 B2 | 2/2008 | Gentil et al. |
| 7,340,772 B2 | 3/2008 | Panasyuk et al. |
| 7,346,842 B1 | 3/2008 | Hayton et al. |
| 7,353,253 B1 | 4/2008 | Zhao |
| 7,359,953 B2 | 4/2008 | Muir et al. |
| 7,376,695 B2 | 5/2008 | Duursma et al. |
| 7,421,484 B2 | 9/2008 | Das |
| 7,444,071 B2 | 10/2008 | Chen |
| 7,453,379 B2 | 11/2008 | Plamondon |
| 7,460,038 B2 | 12/2008 | Samuels et al. |
| 7,490,166 B2 | 2/2009 | Yang et al. |
| 7,496,097 B2 | 2/2009 | Rao et al. |
| 7,502,726 B2 | 3/2009 | Panasyuk et al. |
| 7,502,784 B2 | 3/2009 | Collins |
| 7,529,767 B2 | 5/2009 | DeAnna et al. |
| 7,532,134 B2 | 5/2009 | Samuels et al. |
| 7,542,471 B2 | 6/2009 | Samuels et al. |
| 7,555,529 B2 | 6/2009 | Bloomfield et al. |
| 7,562,121 B2 | 7/2009 | Berisford |
| 7,562,146 B2 | 7/2009 | Panasyuk et al. |
| 7,562,226 B2 | 7/2009 | Aiken et al. |
| 7,565,526 B1 | 7/2009 | Shaw et al. |
| 7,581,005 B2 | 8/2009 | Montemayor et al. |
| 7,584,294 B2 | 9/2009 | Plamondon |
| 7,587,755 B2 | 9/2009 | Kramer |
| 7,593,514 B1 | 9/2009 | Zhuang et al. |
| 7,594,018 B2 | 9/2009 | Pedersen |
| 7,596,593 B2 | 9/2009 | Mitchell et al. |
| 7,606,902 B2 | 10/2009 | Rao et al. |
| 7,609,721 B2 | 10/2009 | Rao et al. |
| 7,613,131 B2 | 11/2009 | Decasper et al. |
| 7,617,531 B1 | 11/2009 | Chauhan et al. |
| 7,619,545 B2 | 11/2009 | Samuels et al. |
| 7,656,799 B2 | 2/2010 | Samuels et al. |
| 7,657,657 B2 | 2/2010 | Rao et al. |
| 7,661,129 B2 | 2/2010 | Panasyuk et al. |
| 7,661,131 B1 | 2/2010 | Shaw et al. |
| 7,664,857 B2 | 2/2010 | Ovsiannikov et al. |
| 7,676,813 B2 | 3/2010 | Bisset et al. |
| 7,831,699 B2 | 11/2010 | Kumar et al. |
| 8,065,397 B2 * | 11/2011 | Taylor .................. G06F 9/4411 709/220 |
| 8,165,893 B1 | 4/2012 | Goldberg et al. |
| 8,260,907 B2 | 9/2012 | O'Sullivan |
| 8,296,413 B2 | 10/2012 | Bornhoevd |
| 8,370,479 B2 | 2/2013 | Hart et al. |
| 8,769,095 B2 | 7/2014 | Hart et al. |
| 8,788,632 B2 | 7/2014 | Taylor et al. |
| 9,491,049 B2 | 11/2016 | Taylor et al. |
| 2001/0007117 A1 | 7/2001 | Cooper et al. |
| 2001/0025377 A1 | 9/2001 | Hinderks |
| 2001/0027439 A1 | 10/2001 | Holtzman et al. |
| 2001/0049690 A1 | 12/2001 | McConnell et al. |
| 2001/0049717 A1 | 12/2001 | Freeman et al. |
| 2001/0052999 A1 | 12/2001 | Hiraoka et al. |
| 2001/0056547 A1 | 12/2001 | Dixon |
| 2002/0006790 A1 | 1/2002 | Blumenstock et al. |
| 2002/0019844 A1 | 2/2002 | Kurowski et al. |
| 2002/0026514 A1 | 2/2002 | Ellis et al. |
| 2002/0032470 A1 | 3/2002 | Linberg |
| 2002/0032720 A1 | 3/2002 | Nelson et al. |
| 2002/0035533 A1 | 3/2002 | Mache et al. |
| 2002/0038320 A1 | 3/2002 | Brook |
| 2002/0052932 A1 | 5/2002 | Curtis et al. |
| 2002/0054169 A1 | 5/2002 | Richardson |
| 2002/0059489 A1 | 5/2002 | Davis et al. |
| 2002/0064138 A1 | 5/2002 | Saito et al. |
| 2002/0078135 A1 | 6/2002 | Venkatsubra |
| 2002/0078259 A1 | 6/2002 | Wendorf et al. |
| 2002/0080391 A1 | 6/2002 | Sugiura et al. |
| 2002/0095600 A1 | 7/2002 | Deen |
| 2002/0116550 A1 | 8/2002 | Hansen |
| 2002/0133753 A1 | 9/2002 | Mayberry et al. |
| 2002/0135801 A1 | 9/2002 | Tessman |
| 2002/0138567 A1 | 9/2002 | Ogawa |
| 2002/0144016 A1 | 10/2002 | Spicer et al. |
| 2002/0157090 A1 | 10/2002 | Anton, Jr. |
| 2002/0174085 A1 | 11/2002 | Nelson et al. |
| 2002/0178241 A1 | 11/2002 | Eriksson |
| 2002/0191612 A1 | 12/2002 | Curtis |
| 2003/0014733 A1 | 1/2003 | Ringseth et al. |
| 2003/0023957 A1 | 1/2003 | Bau et al. |
| 2003/0025931 A1 | 2/2003 | Dorfman et al. |
| 2003/0037148 A1 | 2/2003 | Pedersen |
| 2003/0056140 A1 | 3/2003 | Taylor et al. |
| 2003/0061403 A1 | 3/2003 | Miyata et al. |
| 2003/0063119 A1 | 4/2003 | Bloomfield et al. |
| 2003/0063309 A1 | 4/2003 | Parry |
| 2003/0070006 A1 | 4/2003 | Nadler et al. |
| 2003/0072027 A1 | 4/2003 | Haines et al. |
| 2003/0118353 A1 | 6/2003 | Baller |
| 2003/0154284 A1 | 8/2003 | Bernardin et al. |
| 2003/0158897 A1 | 8/2003 | Ben-Natan et al. |
| 2003/0158919 A1 | 8/2003 | Fomenko |
| 2003/0163569 A1 | 8/2003 | Panasyuk et al. |
| 2003/0177172 A1 | 9/2003 | Duursma et al. |
| 2003/0182375 A1 | 9/2003 | Zhu |
| 2003/0200285 A1 | 10/2003 | Hansen et al. |
| 2003/0200329 A1 | 10/2003 | Delaney |
| 2003/0229529 A1 | 12/2003 | Mui et al. |
| 2003/0229785 A1 | 12/2003 | Daseke et al. |
| 2004/0027376 A1 | 2/2004 | Calder et al. |
| 2004/0030768 A1 | 2/2004 | Krishnamoorthy et al. |
| 2004/0098515 A1 | 5/2004 | Rezvani et al. |
| 2004/0128370 A1 | 7/2004 | Kortright |
| 2004/0139309 A1 | 7/2004 | Gentil et al. |
| 2004/0152450 A1 | 8/2004 | Brasher et al. |
| 2004/0158630 A1 | 8/2004 | Chang et al. |
| 2004/0158631 A1 | 8/2004 | Chang et al. |
| 2004/0177124 A1 | 9/2004 | Hansen |
| 2004/0186693 A1 | 9/2004 | Xiang et al. |
| 2004/0199272 A1 | 10/2004 | Yamamoto |
| 2004/0199792 A1 | 10/2004 | Tan |
| 2004/0210450 A1 | 10/2004 | Atencio et al. |
| 2004/0215605 A1 | 10/2004 | Mester |
| 2004/0221026 A1 | 11/2004 | Dorland |
| 2004/0252628 A1 | 12/2004 | Detzler |
| 2004/0260801 A1 | 12/2004 | Li |
| 2005/0005152 A1 | 1/2005 | Singh et al. |
| 2005/0015501 A1 | 1/2005 | Kaplan et al. |
| 2005/0021772 A1 | 1/2005 | Shedrinski |
| 2005/0033588 A1 | 2/2005 | Ruiz et al. |
| 2005/0044196 A1 | 2/2005 | Pullen et al. |
| 2005/0055397 A1 | 3/2005 | Zhu et al. |
| 2005/0080897 A1 | 4/2005 | Braun et al. |
| 2005/0086172 A1 | 4/2005 | Stefik |
| 2005/0102388 A1 | 5/2005 | Tabbara et al. |
| 2005/0114352 A1 | 5/2005 | Ronneburg |

(56) References Cited

U.S. PATENT DOCUMENTS

| | | |
|---|---|---|
| 2005/0141507 A1 | 6/2005 | Curtis |
| 2005/0144612 A1 | 6/2005 | Wang et al. |
| 2005/0154787 A1 | 7/2005 | Cochran et al. |
| 2005/0182834 A1 | 8/2005 | Black |
| 2005/0190769 A1 | 9/2005 | Smith |
| 2005/0193099 A1 | 9/2005 | Reus et al. |
| 2005/0193386 A1 | 9/2005 | McCaleb et al. |
| 2005/0196023 A1 | 9/2005 | Chen et al. |
| 2005/0198189 A1 | 9/2005 | Robinson et al. |
| 2005/0198245 A1 | 9/2005 | Burgess et al. |
| 2005/0198292 A1 | 9/2005 | Duursma et al. |
| 2005/0198379 A1 | 9/2005 | Panasyuk et al. |
| 2005/0198380 A1 | 9/2005 | Panasyuk et al. |
| 2005/0198393 A1 | 9/2005 | Stutz et al. |
| 2005/0232168 A1 | 10/2005 | Schauser et al. |
| 2005/0235014 A1 | 10/2005 | Schauser et al. |
| 2005/0246445 A1 | 11/2005 | Panasyuk et al. |
| 2005/0246702 A1 | 11/2005 | Yeh et al. |
| 2005/0251551 A1 | 11/2005 | Mitchell et al. |
| 2005/0256614 A1 | 11/2005 | Habermas |
| 2005/0256923 A1 | 11/2005 | Adachi |
| 2005/0262076 A1 | 11/2005 | Voskuil |
| 2005/0267974 A1 | 12/2005 | Panasyuk et al. |
| 2005/0273513 A1 | 12/2005 | Panasyuk et al. |
| 2006/0002315 A1 | 1/2006 | Theurer et al. |
| 2006/0015740 A1 | 1/2006 | Kramer |
| 2006/0029062 A1 | 2/2006 | Rao et al. |
| 2006/0029063 A1 | 2/2006 | Rao et al. |
| 2006/0029064 A1 | 2/2006 | Rao et al. |
| 2006/0031237 A1 | 2/2006 | DeAnna et al. |
| 2006/0031476 A1 | 2/2006 | Mathes et al. |
| 2006/0031779 A1 | 2/2006 | Theurer et al. |
| 2006/0037022 A1 | 2/2006 | Byrd et al. |
| 2006/0037071 A1 | 2/2006 | Rao et al. |
| 2006/0037072 A1 | 2/2006 | Rao et al. |
| 2006/0039354 A1 | 2/2006 | Rao et al. |
| 2006/0039355 A1 | 2/2006 | Rao et al. |
| 2006/0039356 A1 | 2/2006 | Rao et al. |
| 2006/0039404 A1 | 2/2006 | Rao et al. |
| 2006/0047956 A1 | 3/2006 | Calvin |
| 2006/0059239 A1 | 3/2006 | Brasher et al. |
| 2006/0066448 A1 | 3/2006 | Berisford et al. |
| 2006/0069662 A1 | 3/2006 | Laborczfalvi et al. |
| 2006/0069668 A1 | 3/2006 | Braddy et al. |
| 2006/0069683 A1 | 3/2006 | Braddy et al. |
| 2006/0069750 A1 | 3/2006 | Momtchilov et al. |
| 2006/0069753 A1 | 3/2006 | Hu et al. |
| 2006/0070029 A1 | 3/2006 | Laborczfalvi et al. |
| 2006/0070090 A1 | 3/2006 | Gulkis |
| 2006/0070131 A1 | 3/2006 | Braddy et al. |
| 2006/0074837 A1 | 4/2006 | Braddy et al. |
| 2006/0075080 A1 | 4/2006 | Burr et al. |
| 2006/0075114 A1 | 4/2006 | Panasyuk et al. |
| 2006/0075123 A1 | 4/2006 | Burr et al. |
| 2006/0075381 A1 | 4/2006 | Laborczfalvi et al. |
| 2006/0075463 A1 | 4/2006 | Braddy et al. |
| 2006/0077941 A1 | 4/2006 | Alagappan et al. |
| 2006/0087408 A1 | 4/2006 | Korzeniowski |
| 2006/0087409 A1 | 4/2006 | Korzeniowski |
| 2006/0090171 A1 | 4/2006 | Laborczfalvi et al. |
| 2006/0095334 A1 | 5/2006 | Simmons |
| 2006/0095370 A1 | 5/2006 | Seth et al. |
| 2006/0100972 A1 | 5/2006 | Chianese et al. |
| 2006/0130073 A1 | 6/2006 | Faist et al. |
| 2006/0135192 A1 | 6/2006 | Surendra et al. |
| 2006/0150249 A1 | 7/2006 | Gassen et al. |
| 2006/0159080 A1 | 7/2006 | Mazzaferri et al. |
| 2006/0159432 A1 | 7/2006 | Mazzaferri et al. |
| 2006/0161555 A1 | 7/2006 | Mazzaferri et al. |
| 2006/0161671 A1 | 7/2006 | Ryman et al. |
| 2006/0161783 A1 | 7/2006 | Aiken et al. |
| 2006/0161959 A1 | 7/2006 | Ryman et al. |
| 2006/0161974 A1 | 7/2006 | Innes et al. |
| 2006/0179143 A1 | 8/2006 | Walker et al. |
| 2006/0184614 A1 | 8/2006 | Baratto et al. |
| 2006/0190719 A1 | 8/2006 | Rao et al. |
| 2006/0200307 A1 | 9/2006 | Riess |
| 2006/0200494 A1 | 9/2006 | Sparks |
| 2006/0203007 A1 | 9/2006 | Bullard et al. |
| 2006/0206820 A1 | 9/2006 | Bullard et al. |
| 2006/0224742 A1 | 10/2006 | Shabazi et al. |
| 2006/0236325 A1 | 10/2006 | Rao et al. |
| 2006/0236385 A1 | 10/2006 | Innes et al. |
| 2006/0242415 A1 | 10/2006 | Gaylor |
| 2006/0247502 A1 | 11/2006 | Chen |
| 2006/0248144 A1 | 11/2006 | Zhu |
| 2006/0271875 A1 | 11/2006 | Green et al. |
| 2006/0271877 A1 | 11/2006 | Theurer et al. |
| 2006/0282521 A1 | 12/2006 | Anderson et al. |
| 2006/0288119 A1 | 12/2006 | Kim |
| 2007/0005736 A1 | 1/2007 | Hansen et al. |
| 2007/0011295 A1 | 1/2007 | Hansen |
| 2007/0011356 A1 | 1/2007 | Schauser et al. |
| 2007/0022159 A1 | 1/2007 | Zhu |
| 2007/0056009 A1 | 3/2007 | Spilo et al. |
| 2007/0078976 A1 | 4/2007 | Taylor et al. |
| 2007/0088826 A1 | 4/2007 | Raphel et al. |
| 2007/0094076 A1 | 4/2007 | Perkowski et al. |
| 2007/0094672 A1 | 4/2007 | Hayton et al. |
| 2007/0100892 A1 | 5/2007 | Kephart et al. |
| 2007/0106810 A1 | 5/2007 | Ryman |
| 2007/0106811 A1 | 5/2007 | Ryman |
| 2007/0113069 A1 | 5/2007 | Gentil et al. |
| 2007/0124476 A1 | 5/2007 | Oesterreicher |
| 2007/0130167 A1 | 6/2007 | Day et al. |
| 2007/0130337 A1 | 6/2007 | Arinson |
| 2007/0143837 A1 | 6/2007 | Azeez et al. |
| 2007/0150903 A1 | 6/2007 | Hansen |
| 2007/0156810 A1 | 7/2007 | Kumar |
| 2007/0156923 A1 | 7/2007 | Kumar |
| 2007/0157101 A1 | 7/2007 | Indiran et al. |
| 2007/0171921 A1 | 7/2007 | Wookey et al. |
| 2007/0174410 A1 | 7/2007 | Croft et al. |
| 2007/0174429 A1 | 7/2007 | Mazzaferri et al. |
| 2007/0174454 A1 | 7/2007 | Mitchell et al. |
| 2007/0179955 A1 | 8/2007 | Croft et al. |
| 2007/0180447 A1 | 8/2007 | Mazzaferri et al. |
| 2007/0180448 A1 | 8/2007 | Low et al. |
| 2007/0180449 A1 | 8/2007 | Croft et al. |
| 2007/0180450 A1 | 8/2007 | Croft et al. |
| 2007/0180493 A1 | 8/2007 | Croft et al. |
| 2007/0186212 A1 | 8/2007 | Mazzaferri et al. |
| 2007/0192329 A1 | 8/2007 | Croft et al. |
| 2007/0198656 A1 | 8/2007 | Mazzaferri et al. |
| 2007/0198661 A1 | 8/2007 | Hansen |
| 2007/0203952 A1 | 8/2007 | Baron et al. |
| 2007/0239886 A1 | 10/2007 | Montemayor et al. |
| 2007/0271599 A1 | 11/2007 | Rosenstein |
| 2007/0282623 A1 | 12/2007 | Dattorro |
| 2007/0288629 A2 | 12/2007 | Taylor et al. |
| 2007/0294237 A1 | 12/2007 | John et al. |
| 2008/0005321 A1 | 1/2008 | Ma et al. |
| 2008/0031235 A1 | 2/2008 | Harris et al. |
| 2008/0034057 A1 | 2/2008 | Kumar et al. |
| 2008/0034072 A1 | 2/2008 | He et al. |
| 2008/0034110 A1 | 2/2008 | Suganthi et al. |
| 2008/0034111 A1 | 2/2008 | Kamath et al. |
| 2008/0034119 A1 | 2/2008 | Verzunov et al. |
| 2008/0034410 A1 | 2/2008 | Udupa et al. |
| 2008/0034413 A1 | 2/2008 | He et al. |
| 2008/0034418 A1 | 2/2008 | Venkatraman et al. |
| 2008/0034419 A1 | 2/2008 | Mullick et al. |
| 2008/0043617 A1 | 2/2008 | Schekochikhin et al. |
| 2008/0043622 A1 | 2/2008 | Kamath et al. |
| 2008/0043749 A1 | 2/2008 | Suganthi et al. |
| 2008/0043760 A1 | 2/2008 | Venkatraman et al. |
| 2008/0043761 A1 | 2/2008 | Kumar et al. |
| 2008/0046371 A1 | 2/2008 | He et al. |
| 2008/0046616 A1 | 2/2008 | Verzunov et al. |
| 2008/0046714 A1 | 2/2008 | Suganthi et al. |
| 2008/0046717 A1 | 2/2008 | Kanekar et al. |
| 2008/0046727 A1 | 2/2008 | Kanekar et al. |
| 2008/0046994 A1 | 2/2008 | Venkatraman et al. |
| 2008/0049616 A1 | 2/2008 | Kamath et al. |

(56) References Cited

U.S. PATENT DOCUMENTS

| | | |
|---|---|---|
| 2008/0065757 A1 | 3/2008 | Motoyama et al. |
| 2008/0068289 A1 | 3/2008 | Piasecki |
| 2008/0068290 A1 | 3/2008 | Muklashy et al. |
| 2008/0069005 A1 | 3/2008 | von Eicken et al. |
| 2008/0069104 A1 | 3/2008 | von Eicken et al. |
| 2008/0071905 A1 | 3/2008 | Sullivan et al. |
| 2008/0082657 A1 | 4/2008 | Hart et al. |
| 2008/0109912 A1 | 5/2008 | Rivera |
| 2008/0126978 A1 | 5/2008 | Bai et al. |
| 2008/0154409 A1 | 6/2008 | Srikumar et al. |
| 2008/0154957 A1 | 6/2008 | Taylor et al. |
| 2008/0201405 A1 | 8/2008 | Duursma et al. |
| 2008/0208605 A1 | 8/2008 | Sinha et al. |
| 2008/0219122 A1 | 9/2008 | Detzler et al. |
| 2008/0231414 A1 | 9/2008 | Canosa |
| 2008/0250110 A1 | 10/2008 | Zhao |
| 2009/0013064 A1 | 1/2009 | Taylor et al. |
| 2009/0019226 A1 | 1/2009 | Edwards et al. |
| 2009/0055745 A1 | 2/2009 | Christiansen |
| 2009/0064134 A1 | 3/2009 | Cox |
| 2009/0099836 A1 | 4/2009 | Jacobsen et al. |
| 2009/0100349 A1 | 4/2009 | Hancock et al. |
| 2009/0106347 A1 | 4/2009 | Harwood et al. |
| 2009/0117890 A1 | 5/2009 | Jacobsen et al. |
| 2009/0119408 A1 | 5/2009 | Teze et al. |
| 2009/0187654 A1 | 7/2009 | Raja et al. |
| 2009/0234972 A1 | 9/2009 | Raghu et al. |
| 2009/0259728 A1 | 10/2009 | Berisford et al. |
| 2012/0117203 A1 | 5/2012 | Taylor et al. |
| 2013/0179565 A1 | 7/2013 | Hart et al. |
| 2015/0032882 A1 | 1/2015 | Hart et al. |
| 2015/0074248 A1 | 3/2015 | Taylor et al. |

FOREIGN PATENT DOCUMENTS

| | | |
|---|---|---|
| EP | 1 362 282 | 11/2003 |
| EP | 1 695 485 | 8/2006 |
| FR | 2797728 | 2/2001 |
| GB | 2305820 | 4/1997 |
| JP | 60-263162 | 12/1985 |
| JP | 06-062130 | 3/1994 |
| JP | 07-325513 | 12/1995 |
| JP | 09-163008 | 6/1997 |
| JP | 09-305407 | 11/1997 |
| JP | 09-325925 | 12/1997 |
| JP | 10-190922 | 7/1998 |
| JP | 10-224372 | 8/1998 |
| JP | 11-203079 | 7/1999 |
| JP | 11-296453 | 10/1999 |
| JP | 2000-112863 | 4/2000 |
| JP | 2000-122952 | 4/2000 |
| JP | 2000-278773 | 10/2000 |
| JP | 2000-309145 | 11/2000 |
| JP | 2001-337817 | 12/2001 |
| JP | 2003-223603 | 8/2003 |
| WO | WO97/30879 | 8/1997 |
| WO | WO98/20439 | 5/1998 |
| WO | WO98/33302 | 7/1998 |
| WO | WO98/38910 | 9/1998 |
| WO | WO98/41943 | 9/1998 |
| WO | WO99/21336 | 4/1999 |
| WO | WO99/57649 | 11/1999 |
| WO | WO99/57837 | 11/1999 |
| WO | WO99/57838 | 11/1999 |
| WO | WO99/64958 | 12/1999 |
| WO | WO00/23894 | 4/2000 |
| WO | WO02/10919 | 2/2002 |
| WO | WO02/21239 | 3/2002 |
| WO | WO02/21299 | 3/2002 |
| WO | WO02/21414 | 3/2002 |
| WO | WO02/21415 | 3/2002 |
| WO | WO02/21777 | 3/2002 |
| WO | WO02/25501 | 3/2002 |
| WO | WO03/021464 | 3/2003 |
| WO | WO03/054439 | 7/2003 |
| WO | WO2004/059447 | 7/2004 |
| WO | WO2006/009402 | 1/2006 |
| WO | WO2008/083177 | 7/2008 |

OTHER PUBLICATIONS

24×7, HealthTech Publishing Company, Inc. (Nov. 1996).
"Remote Diagnostics: Strategic weapon in the war for multi-vendor service contracts," Tech Assessment, vol. 3, No. 12, Dec. 1995.
"Siemens Medical, BJC Health System Extend deal to multivendor service," Medical Imaging News, vol. 6, No. 26, Jun. 27, 1997.
Dec. 27, 1995, SCAN Diagnostic Imaging, vol. 8, No. 24.
Apr. 22, 2005 Literature Search by Keyword: CyberTAC.
Adelberg, D., "Building Robust Wrappers for Text Sources", [online] Retrieved from the Internet:<URL:http://student.bu.ac.bd/~mumit/Research/NLP-bib/papers/Adelberg99.pdf> [retrieved on Nov. 24, 2008] (1999).
Allegro Software product release 1-61 overview Greenhills Software Inc., [online] Jun. 10, 2002 (Jun. 10, 2002), pp. 1-1, XPOO2201939 Retrieved from the Internet: <URL: http://www.ghs.com/partners/allegro/> [retrieved on Jun. 10, 2002] the whole document.
Allegro, RomWebCLient Embedded HTTP client Toolkit: Allegrosoft, Circuit Cellar Online, Sep. 7, 2000, pp. 1-2, XP-002201983, URL:http://web.archive.orgweb/20000709204234/ http://www.allegrosoft.com/romwebclient.html.
Bock, G., "Mainstreaming XML-based Enterprise Applications: Using Oracle XML DB to Manage Financial Information within a Global Banking System", Oracle Corporation, (C) 2003.
Box, et al., Simple Object Acces Protocol (SOAP) 1.1, Document No. XP002250270, May 8, 2000.
Chandler, T. et al., "The Technology Development of Automatic Metering and Monitoring Systems", Int'l Power Engineering Conf. 2005, IEEE, 4 pgs.
Cheung, D. et al., "Distributed and Scalable XML Document Processing Architecture for E-Commerce Systems", Adv. Issues of E-Commerce and Web-Based Information Systems, WECWIS 2000, 2nd Int'l Workshop, (Jun. 2000), pp. 152-157.
Ennis, D., "CORBA and XML Integration in Enterprise Systems", IONA Technologies Inc. [online], Retrieved from the Internet: <URL: http://citeseer.ist.psu.edu/cache/papers/cs/16013/ http:zSzzSzwww.iona.comzSzinfozSztechcenterzSzecoop2000apr17.pdf/ennis00corba.pdf> [retrieved on Nov. 24, 2008] (2000).
CyberTAC & RadScape Presentation (May 1997).
CyberTAC Design Presentation (1997).
CyberTAC from Virtual Impact Systems, Inc. Presentation (1997).
CyberTAC Remote Support System Presentation (1997).
Database WIP, Section EI, Week 200156, Abstract, Document No. XP002253876 (Korea Electronics & Telecom Res Inst.) Derwent Publications, Ltd., London, GB, (Mar. 2001).
Eastvold, Roger, "Services: The Next Generation," The Professional Journal, vol. 20, No. 4.
Eastvold, Roger, "Tiss and Tell," Medical Imaging, Sep. 1995.
EBITS:Electronic Business & Information Technology for Society Research Consortium, Proposal for Development of an Educational and Research Infrastructure for Safe Electronic Commerce, [online] Retrieved from the Internet:<URL:http://www.cs.dartmouth.edu/~makedon/cs188/proposal.html>, [retrieved Feb. 15, 2005].
Jiang, et al., "Record-Boundary Discovery in Web Documents", [online] Retrieved from the Internet:<URL:http://osm7.cs.byu.edu/deg/papers/SJ.Thesis.ps>, [retrieved on Nov. 24, 2008] (1998).
Emmerich et al., Implementing Incremental Code Migration with XML, IEEE, 4-11, (Jun. 2000).
EmWare Press Release: "emWare Announces Support for Sun Microsystems Jini Technology," Salt Lake City, UT (Feb. 1999).
EmWare Press Release: "emWare Delivers EMIT 3.0 SDK Pro—A Complete Device Networking Kit for Developing End-to-end, Embedded Device Networking Solutions," Salt Lake City, UT (May 1999).

(56) References Cited

OTHER PUBLICATIONS

EmWare Press Release: "emWare, IBM Demonstrate Next Phase in Establishing Worldwide Access to Embedded Devices," Chicago, IL (Mar. 1999).

EmWare Press Release: "emWare's emLink (TM) Used to Internet-enable Welch Allyn's Vital Signs Monitor," Chicago, IL (Mar. 1999).

EmWare Press Release: "Invensys Selects emWare EMIT Device-Networking Software to Add Remote Monitoring and Control Capabilities to its Controller Products," Salt Lake City, UT (Jun. 1999).

EmWare Press Release: "Motorola, Mitsubishi and National Semiconductor Join emWare's Embed The Internet Alliance," Chicago, IL (Mar. 1999).

Franklin, M. et al., "Data in Your Face: PUSH Technology in Perspective", Proc. ACM SIGMOD Int'l Conf. on Mgmt of Data, (Jun. 1998), #XP000886180, pp. 516-519.

Hanckmann, J., "Telescript: The Emerging Standard for Intelligent Messaging," Philips Telecommunications Review, vol. 52(1), pp. 15-19 (Mar. 1994).

Universal Plug & Play Device Architecture, (C) Microsoft Corporation (Jun. 8, 2000), [online] Retrieved from the Internet: <URL:http://www.upnp.org/specs/arch/upnpda10_20000613.htm>, [retrieved on Nov. 24, 2008].

Incremona, A. "Remote Service Diagnostics for Imaging Equipment: Today and Tomorrow," Advanced Imaging, 12(9):90(2) (1997).

Jennyc, Kenn S., "Linking Enterprise Business Systems to the Factory Floor," The Hewlett-Packard Journal, Article 9 (May 1998).

Kafeza, E. et al., "Alerts in Mobile Healthcare Applications: Requirements and Pilot Study", IEEE, vol. 8, No. 2, pp. 173-181 (Jun. 2004).

Kimball, R., "XML Will Make it Easier," Intelligent Enterprise, [online] Retrieved from the Internet:<URL:http://www.intelligententerprise.com/010416/webhouse1_1.jhtml> [retrieved on Nov. 24, 2008] (Apr. 16, 2001).

Koppen, E., et al., "Active Hypertext for Distributed Web Applications", Enabling Technologies: Infrastructure for Collaborative Enterprises, (WET ICE '99), Proc. IEEE 8th Int'l. Workshop (1999), pp. 297-302.

Kovar, J., "Xerox Unveils Expanded Channel Lineup; Also Plans to Introduce E-Mail, Queue Management Software," PC Expo,(Jun. 1999).

Lassman, M. et al., "Modern Nuclear Medical Diagnostics with Efficient Gamma Cameras," Electromedica, 66(2):43-51, (1998).

Lewandowska, J., et al., "System for Grouping Technologically Similar Devices", v. 48 n 12; (Dec. 1975), pp. 636-638 (English Abstract).

Layman, et al., "XML-Data," Position Paper from Microsoft Corp. (Jun. 1997), [online] Retrieved from the Internet:<URL:http://www.oasis-open.org/cover/xml-data9706223.html> [retrieved on Sep. 2, 2004].

Lerner, R., "At the Forge: Introducing SOAP", Linux Journal, #XP002292162 (Mar. 2001).

Lindley, D., "Xerox unveils copier that phones for help," Rochester Democrat and Chronicle, (Mar. 28, 1990).

Luh, James C., "With several specs complete, XML enters widespread development," Internet World, (Jan. 4, 1999).

Martin, D., "Protessional XML"., WROX Press Ltd., pub., Ch. 11, 'Server to Server', pp. 559-562, 819-820 (2000).

Mason, K. "XML Translation for block structured languages", IBM Corporation: Research Disclosure, Kenneth Mason Publications, 44176 (2001).

Math Markup Language (Chapter 4); [online] Retrieved from the Internet:<URL:http://www.w3.org/TR/REC-MathML/chap4_4.html>, [retrieved on Feb. 15, 2005].

McBride, R.A., "Security Considerations for Active Messages," ACM SIGICE Bulletin, vol. 22 (2), (Oct. 1996).

Memphis Educational Computer Connectivity Alliance (MECCA), [online] Retrieved from the Internet:<URL:http://www.mecca.org/~ltague/nsfnocostextension.html>, [retrieved on Feb. 15, 2005].

Mills et al., "A knowledge-based method for inferring semantic concepts from visual models of system behavior," ACM (Jul. 2000), pp. 306-337.

Orasis Medical Services, Inc., Business Plan Copy No. 001, (Nov. 1995).

Pfeiffer, R., "XML Tutorials for Programmers: Tutorial 2: Writing XML Documents," (1999) [online] Retrieved from the Internet:<URL:http://imb.com/xml>, [retrieved on Mar. 2, 1999].

Questra Applications Data Sheet (2002).

Questra Preliminary Invalidity Contentions, dated Apr. 29, 2005.

Reagan, K., "Technology for the Soul," OC Metro, (Sep. 1, 1995).

Rytting, T., "Dispensing the Goods, Embedded Style," Circuit Cellar Online, (Oct. 1999).

Schmidt, The Evolution of Workflow Standards, IEEE (1999).

SOAP Archives Online, "Multiple Method Calls in SOAP Packet"; [online] Retrieved from the Internet:<URL:http://discuss.develop.com/archives/wa.exe?A2=ind9912&L=soap&T=O&F=&S=&P=25113>, [retrieved on Dec. 8, 2000].

Steinfeld, E., "From Standalone to Internet Appliance", Circuit Cellar Online, [online] (Jul. 9, 2000), #XP002201938, Retrieved from the Internet: <URL:http://web.archive.org/web/20000709204234/http://www.alegrosoft.com/romwebclient.html>retrieved on Jun. 12, 2002 the whole document.

Steinfeld, E., "Internet-appliance technology automates test equipment" EDN Magazine, pp. 157-169, Oct. 2000, www.edbmag.com.

Suresh et al., "XML-based Data System for Earth Science Applications", IEEE 2000 International, vol. 3, pp. 242-28, Jul. 2000.

Searls, "The Next Bang: The Explosive Combination of Embedded Linux, XML, and Instant Mess.", ACM (Sep. 2000) Issue 77 [online] Retrieved from the Internet:<URL:http://www.linuxjournal.com/article.php?sid=4195>, [retrieved on Nov. 20, 2001].

The Simple Times, vol. 7, No. 1, Mar. 1999; [online] Retrieved from the Internet:<URL:http://www.simple-times.org/pub/simple-times/issues/7-1.html> [retrieved on Aug. 3, 2005].

Trewitt, G., "Using Tcl to Process HTML Forms," Digital Network Systems Laboratory, NSL Technical Note TN-14, Palo Alto, CA (Mar. 1994).

Virtual Reality Transfer Protocol (VRTP); Retrieved from the Internet:<URL:http://www.stl.nps.navy.mil/~brutzman/vrtp> (1998).

Walsh, Norman, "XSL The Extensible Style Language: Styling XML Documents," New Architect Daily, Jan. 1999.

Webmethods B2B Whitepaper; [online] Retrieved from the Internet:<URL:http://www.cs.wisc.edu/~vganti/papers/b2b_wpB2Bintegration.html> (1999).

White Paper, Medical Imaging, East Providence, RI (Sep. 1995).

Wigget, Jeremy, "Intraview: Roger Eastvold of Orasis Inc.," 24×7, Nov. 1996.

Williams, T., "Java Goes to Work Controlling Networked Embedded Systems" Computer Design, Pennwell Publ. Littleton, MA, 35:9:36-37, Aug. 1996.

Winer, Dave, "XML-RPC Specification," (http://XML-RPC.com), Jun. 15, 1999.

Winter 1992, Field of View, vol. 2, No. 3, Toshiba America Medical System, Inc.

Wu et al., "A knowledge sharing and collaboration system model based on Internet", Systems, Man, and Cybernetics, 1999. IEEE SMC'99 Conference Proceedings, vol. 2, pp. 148-152 (1999).

Xerox 190 Copier, Electronic Data Interface Operator Guide, ver. 1.0, (1989).

Van der Werff, M., et al., "A Mobile-Based Home Automatic System", IEEE Mobility Conference (2005).

Defense Information Systems Agency, Field Services Office, White Paper Report "pcAnywhere 10.5" (Sep. 2003).

Examination Report in EP Application No. 01955993.9, dated Jan. 29, 2004.

Examination Report in EP Application No. 01955993.9, dated Aug. 5, 2004.

(56) References Cited

OTHER PUBLICATIONS

Examination Report in EP Application No. 01955993.9, dated Dec. 16, 2004.
Examination Report in EP Application No. 01973431.8, dated Mar. 8, 2005.
Communication in EP Application No. 01973431.8, dated Mar. 30, 2005.
Examination Report in EP Application No. 01973431.8, dated Jan. 15, 2008.
Office Action in EP Application No. 01996048.3, dated Jun. 22, 2004.
Office Action in EP Application No. 01996048.3, dated Mar. 11, 2005.
Office Action in EP Application No. 01955993.9, dated Jun. 6, 2005.
Examination Report in EP Application No. 03719774.6, dated Sep. 12, 2005.
Examination Report in EP Application No. 03719774.6, dated Apr. 12, 2006.
Examination Report in EP Application No. 01973431.8, dated Feb. 6, 2009.
Search Report in EP Application No. 02792391.1, dated Nov. 19, 2009.
Examination Report in EP Application No. 01973431.8, dated Mar. 23, 2010.
Examination Report in EP Application No. 02792391.1, dated Mar. 10, 2010.
Response to Examination Report in EP Application No. 01973431.8, dated Oct. 4, 2010.
Letter from Foreign Associate regarding response filed in EP Application No. 01973431.8, dated Oct. 8, 2010.
English translation of Notification of Reasons for Refusal in Japanese Application No. 2002-529431, dated Nov. 8, 2010.
Notice of Reasons for Rejection in Japanese Application No. 2002-529431, dated Nov. 8, 2010.
Machine Translation of Japanese Patent Publication No. 09-305407 (Pub Date Nov. 1997).
Machine Translation of Japanese Patent Publication No. 11-296453, (Pub Date Oct. 1999).
Machine Translation of Japanese Patent Publication No. 11-203079, (Pub Date Jul. 1999).
Machine Translation of Japanese Patent Publication No. 2001-337817, (Pub Date Dec. 2001).
Machine Translation of Japanese Application No. 2000-122952, (Pub Date Apr. 2000).
International Search Report in Application No. PCT/US2002/040058, dated Nov. 3, 2003.
International Preliminary Examination Report in Application No. PCT/US2002/040058, dated Jun. 10, 2004.
International Search Report in Application No. PCT/US01/23651, dated Jun. 3, 2002.
International Search Report in Application No. PCT/US01/29787, dated Jun. 28, 2002.
International Preliminary Examination Report in Application No. PCT/US01/29787, dated Aug. 21, 2002.
International Preliminary Examination Report in Application No. PCT/US01/23651, dated Oct. 10, 2002.
International Search Report in Application No. PCT/US01/45198, dated Apr. 29, 2003.
International Search Report in Application No. PCT/US03/11707, dated Sep. 24, 2003.
International Search Report and Written Opinion in Application No. PCT/US03/11701, dated Oct. 13, 2004.
Written Opinion in Application No. PCT/US01/45198, dated May 31, 2007.
International Preliminary Examination Report in Application No. PCT/US01/45198, dated Apr. 2, 2008.
International Preliminary Report on Patentability (incl. Written Opinion) in Application No. PCT/US2007/088858, dated Jul. 9, 2009.
International Search Report &. Written Opinion in Application No. PCT/US2007/088858, dated May 21, 2008.
Summons to attend Oral Proceedings in counterpart EP Application No. 01973431.8, dated Feb. 2, 2011.
Second Auxiliary Response in EP Application No. 01973431.8, dated Apr. 26, 2011.
Summons to attend oral proceedings in corresponding European Application No. 01955993.9 dated Oct. 31, 2005.
Result of Consultation of Nov. 24, 2005 and Nov. 25, 2005 from corresponding European Application No. 01955993.
Submission in German dated Nov. 25, 2005 from corresponding European Application No. 01955993.9.
Annex to EPO Form 2004 with claims for grant in European Application No. 01955993.9 (Nov. 29, 2005).
Oral Proceeding Minutes in European Application No. 01955993.9, dated Jan. 16, 2006.
Communication dated Apr. 26, 2005 in European Application No. 01955993.9.
Al-Shaer, Ehab, "A dynamic group management framework for large-scale distributed event monitoring" [Online] 2001 Retrieved on Feb. 5, 2014, IEEE/IFIP International Symposium on Integrated Network Management Proceedings, pp. 361-374 [Retrieved from: http://ieeexplore.ieee.org/stamp/stamp.jsp?tp=&arnumber=918053].
Notice of allowance from U.S. Appl. No. 13/727,097 mailed Feb. 20, 2014 (59 pages).
IBM Technical Disclosure Bulletin, "Dynamic icon Navigation to Nested Containers", vol. 34, No. 8, pp. 386-388, Jan. 1992.
Prosecution History of U.S. Pat. No. 8,370,479 (Aug. 18, 2015).
Prosecution history of U.S. Pat. No. 8,769,095 (downloaded Aug. 18, 2015).
Prosecution History of U.S. Pat. No. 8,788,632 (downloaded Aug. 18, 2015).
Prosecution History of U.S. Pat. No. 8,065,397 (downloaded Aug. 18, 2015).
Non Final Office action issued in U.S. Appl. No. 14/317,151 on Sep. 15, 2015 (29 pages).
Office Action for U.S. Appl. No. 11/616,136, 11 pages (Apr. 2, 2010).
Office Action for U.S. Appl. No. 11/616,136, 6 pages (Dec. 27, 2010).
Office Action for U.S. Appl. No. 14/335,428, 5 pages (Mar. 11, 2015).

\* cited by examiner

MANAGING CONFIGURATIONS OF DISTRIBUTED DEVICES

CROSS-REFERENCE TO RELATED APPLICATIONS

This application is a continuation (and claims the benefit of priority under 35 U.S.C. §120) of U.S. application Ser. No. 14/335,428, which was filed Jul. 18, 2014 and which is a continuation (and claims the benefit of priority under 35 U.S.C. §120) of U.S. application Ser. No. 13/252,357 (issued as U.S. Pat. No. 8,788,632 on Jul. 22, 2014), which was filed Oct. 4, 2011 and which is a continuation (and claims the benefit of priority under 35 U.S.C. §120) of U.S. application Ser. No. 11/616,136 (issued as U.S. Pat. No. 8,065,397 on Nov. 22, 2011), which was filed Dec. 26, 2006. The disclosures of each of the prior applications (U.S. application Ser. Nos. 14/335,428, 13/252,357 and 11/616,136) are considered part of (and are incorporated by reference in) the disclosure of this application as if set forth herein in full.

BACKGROUND

Field of the Art

The present disclosure generally relates to configuration management databases and, more particularly, to systems and methods for managing configurations of distributed devices.

Background and Relevant Art

Over time, device manufactures produce many configurations of a given product line as features are added and defects are addressed. Manufactures need to know the configuration of the devices to be able to support the components and provide the proper "upgrade" path. The configurations of these devices are changed in the field as customers, users, or technicians update hardware and software components. The ability to track the configuration of the devices becomes more complex when the device has been in the field for a long period of time. For example, the life of a CT scanner or X-Ray machine can typically be about 10 to 20 years.

Some devices are regulated by the FDA. When updating hardware or software on the regulated devices, the FDA mandates tracking the configuration of certain devices and recording software updates. Records are required, for example, on medical devices that track these updates. Various methods have been used to track updates, ranging from an entire paper system to homegrown systems implemented to track devices in an enterprise resource planning (ERP) system as part of software bill of materials (BOM). May manufacturers do not trust the data collected in these systems since the data accuracy relies on the service technician to properly update the device records, which may or may not occur. Sometimes service technicians update devices that were not scheduled to be updated, which further compounds the problems. Another complicating factor is that some end-customers have the ability to apply updates to the device (e.g., when CDs are shipped by the manufacturer), which leaves the manufacturer to rely on the customer or service technician to report on the status of each update. And on some devices, all control is lost by the manufacturer when the end-customers have the ability to update, add, and/or remove software.

Databases have been implemented to store relevant information about the devices in an organization's information technology (IT) services and to store the relationships between those components. This type of database is typically referred to as a configuration management database (CMDB). A CMDB generally organizes data collected from the components into a way that can be viewed and examined from various perspectives. The components of the information system in this context are referred to as configuration items (CI). The CI can include software, hardware, documentation, personnel, and any other conceivable IT component or combination of components.

U.S. Patent Application Publication No. 2005/0193386 to MaCaleb et al discloses a method for remotely updating software in computer systems. In the method, a client computer sent information about a software application to a server. The server compared the information to the most-updated upgrade package for the software application, which is stored in a part database. When the most up-to-date upgrade package was not installed, the upgrade was automatically sent to the client system. A client database stored configuration files for the client systems, which included a list of the installed software applications and their versions. MaCaleb discloses a "smart" creation of an update based on the "latest version" of components in the parts database. This system does not maintain information about the configuration of the device, but uses it to determine the delta from the latest. This system also does not verify that the update will match the configuration of the hardware and software associated with the device.

In U.S. Patent Application Publication No. 2005/0262076 to Voskuil, a computer system is disclosed that is configured for policy-based management of software updates. The system maintained group-policy objects, with which groups of computers are associated. The system obtained identities of software updates from a source and filter criteria for each update to determine whether the update should be applied to a particular computer. The system assigned newly available updates to selected group-policy objects and added the obtained filter criteria to each group-policy object. The system performed necessary update installations for each group-policy object by determining whether the computer satisfied the filter criteria for the update for each combination of a computer belonging to a group associated with that policy object and an update assigned to that policy object. If so, the system applied the update to that computer. Although this system checks whether the update should be applied to a particular computer by applying filter criteria, it does not verify the configuration criteria. This system uses group policies to control software updates.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF THE INVENTION

A method manages configurations of devices in a system that communicates information between a device and an enterprise. The method includes building defined configurations for a device type. The defined configuration includes a set of value requirements. An actual configuration of the device is compared to the defined configuration. The actual configuration and defined configuration are stored in a database of the enterprise. The actual configuration has values associated with the device. The method also includes determining, in the enterprise, if the values of actual configuration match the corresponding values of the defined configuration. The method runs business logic associated with the device based on a result from the step of determining if the values of the actual configuration match the corresponding values of the defined configurations. The matched configurations are stored for subsequent evaluation.

In another aspect of the invention, a system manages configurations of a device associated with a monitor agent. The system includes a server that communicates with the monitor agent. The monitor agent is configured to collect information from the device to obtain an actual configuration of the device. A database is configured to store the actual configuration of the device and a defined configuration of a device type. The device type is associated with a set of devices. The defined configuration is built for the device type and stored in the database. The defined configuration includes a set of value requirements. The actual configuration has values associated with the device. An enterprise is configured to compare the actual configuration to the defined configuration and to determine whether the values of the actual configuration match the corresponding values of the defined configuration. The enterprise is configured to store the matching defined configuration and running business logic associated with the device based on a result from the comparison between the values of the actual configuration and the corresponding values of the defined configuration.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more frilly apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION OF THE INVENTION

Figure 1:
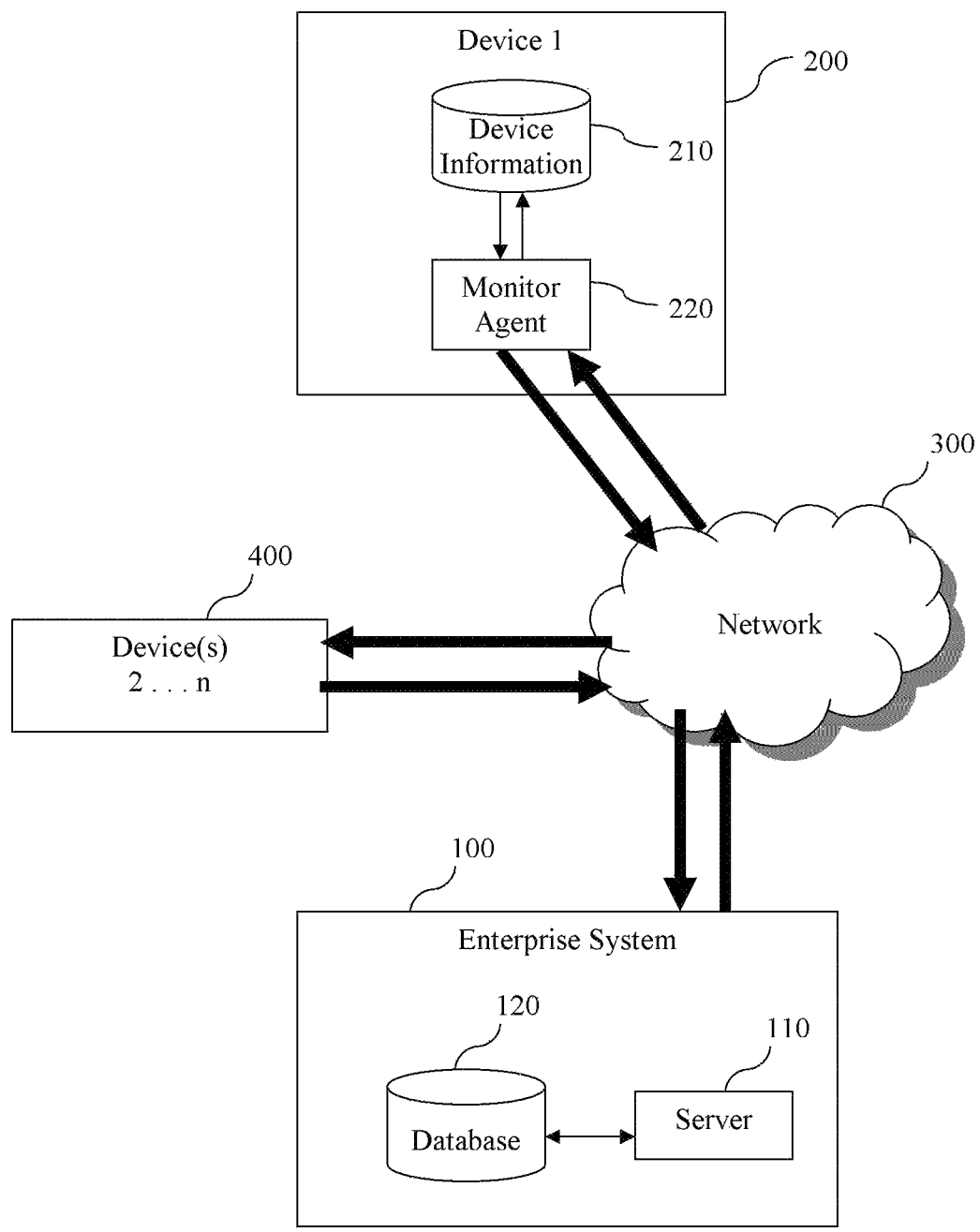
FIG. 1 illustrates a system managing configurations of distributed devices in accordance with the various embodiments of the present invention.

The present system and method includes various embodiments for managing configurations of distributed devices. A configuration management database (CMDB) is configured to manage configuration items (CI) of devices. The CMDB tracks and validates the software and hardware used by the device. The system also tracks the device configuration, including the state of that configuration and can take an appropriate business action. A business action, for instance, can include sending a technician out to a site to update the hardware, such as memory, or complete another action, such as sending a software update or collecting data.

In one exemplary embodiment of the system, the CMDB updates the devices with controlled installations over its lifetime to help assure that the device will operate safely after an update installation. Before an update is sent to the device, the CMDB verifies that it is compatible with a defined configuration of the device, which is stored in the CMDB. If the device is not compatible, a business action can occur before the update is sent to the device since the configuration is known. The system can also allow remote updates to the software and/or the device configuration. The "latest" configuration of the device may not necessarily be the only valid configuration and may require changes to the configuration to match a given update. The business logic can take place soon after the comparison or at a later time. The devices, for example, can be regrouped for later action. The comparison matches are stored in the enterprise so that it can take future action with the devices even if the action takes place days or weeks later.

An IT department for a large corporation may have many thousands of devices to manage on a corporate network, such as server computers, desktop computers, laptops, firewalls, routers, switches, and the like. IT departments, especially for large corporations, may have problems trying to track the configurations of each device. Device configurations need to be managed efficiently to be able to handle numerous devices. While the device management problem is similar to the IT problem, the complexity of managing devices beyond the corporate network or a network not owned by the service provider and the expected lifetime of the device makes this problem more complex.

The present invention includes many advantages. Device manufactures will be able to automatically track and manage device configurations to safely update the devices in the field. In addition, the system will streamline device support and service to benefit businesses, for instance, by reducing costs and improving customer satisfaction. The process is streamlined by driving entitlement validation and expediting problem diagnosis. Furthermore, the system reduces the time it takes to launch a product in the marketplace by improving the time and ability to meet regulatory requirements.

In one application of the invention, for example, the system can be used to track medical devices that are regulated by the FDA. Regulated devices often require the manufacturer to record device configurations in the event that an important or even dangerous defect is found. The FDA regulates tracking and updating methods for medical devices to insure quick handling of defects that could cause potential safety issues. It is important to know the current device configuration before software or configuration updates are delivered. The present invention provides a way for the user that installs the update to know that the update is compliant with the device and that the device will operate safely after the installation.

A common methodology for dealing with the configuration management problem in the IT space is called IT Infrastructure Library (ITIL). The present invention builds on the ITIL Configuration Management to deal with the issues raised by device manufacturers.

The system uses Configuration Management. The process identifies and defines CI in a system, records and reports the status of the CI and Requests for Change, and verifies the completeness and correctness of the CI. The CI is a component of an infrastructure—or an item, such as a Request for Change, associated with an infrastructure—which is or will be under the control of Configuration Management. The CI may vary widely in complexity, size, and type, from an entire system, including hardware, software, and documentation, to a single module or minor hardware component. The CMDB contains relevant details of each CI and details of the relationships between the CI.

As shown in FIG. 1, the system can include an enterprise system 100 that communicates with at least one device 200 through a local or global computer network 300, such as the Internet, World Wide Web, or other similar network. The enterprise system 100 includes a server 110 that is connected to a database 120, such as a CMDB. The device 200 communicates with the enterprise 100 at predefined intervals. The device, for instance, can include a power meter, MRI machine, printing press, X-Ray machine, or other devices that include, or can be adapted to include, a monitor agent. These devices may vary in complexity and may have a set of subsystems associated with them.

The device 200 contains or is connected through a serial port, USB, network, or the like to a monitor agent 220. The monitor agent 220 is configured to monitor the device status and verify that the device is properly functioning and maintained. The monitor agent 220 communicates device information to the enterprise 100 as requested by enterprise users or when monitored conditions are met, as defined by rules. The rules can include monitoring rules, which are set up by the user in the monitor agent 220 on the device side, or dynamic group rules, which are set up by the enterprise user to monitor an active status of the devices that belong to the defined group. The status includes operational status, data readings, or configuration of the device.

Other devices 400 can be connected to the enterprise system 100 through the network 300, such as the global computer network or other local network. The devices 400 are represented as systems 2 through n to mean any defined amount of devices, which can meet, but not exceed, the capacity of the enterprise system 100. As the users' needs grow, the enterprise system 100 can be modified to match the users' needs, for example, by adding more bandwidth, servers, and/or database capacity. Each of the other devices 400 includes similar components as those defined in the device 200.

The monitor agent 220 collects information from the sources of device data, such as a database, a registry, the file system, or data collection protocols. The type of data can include various classes of information including: monitoring data, usage data, and configuration data. This data, for example, can include the operational status, operational data, usage information, location information, environmental information, SW/HW version information (i.e. "configuration" information), or any data available on the device that can be communicated to the enterprise 100. To collect the data, the monitor agent 220 uses plug-in modules to collect device information using either standard or device-proprietary methods. The monitor agent 220 sends data to the enterprise using Web services. The software is not limited to a specific protocol such as simple mail transfer protocol (SMTP) or hypertext transfer protocol (HTTP) but may be adapted to any protocol known by one skilled in the art for data interchange at the hardware device level or at application program level.

The monitor agent 220 can send data sets of information to an enterprise server at the time of a triggering event, and just before and after the event, to capture the condition of the device to provide a baseline. The data can also be collected at a specific time, such as every evening or at the close of business. Each time the device is updated or software revisions are installed, the data also can be collected. If the user needs information outside the prescribed times, a user request can be sent at any time. For instance, if a user wants to verify the configuration of the device and does not want to wait for a prescribed time, a request can be sent immediately.

The communication between the enterprise 100 and the monitor agent 220 can be rejected due to firewalls, NAT, etc. that are implemented to block unwanted communication. The system can use a "polling server" model to enhance the ability to communication between the device and the enterprise if needed. The "polling server" model is discussed, for example, in U.S. Patent Publication No. 2003/0118353 entitled Method and Apparatus for Managing Intelligent Assets in a Distributed Environment, which is hereby incorporated by reference in its entirety.

When collecting data from a device, the CMDB collects a configuration baseline. The baseline is a configuration of a product or system established at a specific point in time, which captures both the structure and details of that product or system, and enables that product or system to be rebuilt at a later date. The baseline records a snapshot or a position of the data. Although the position may be updated later, the baseline remains unchanged and available as a reference of the original state and as a comparison against the current position of the device. The CMDB collects and stores the actual configuration of a device.

The CMDB also stores one or more defined configurations for each device type. The defined configuration is a set of elements that describe the value requirements. The element can include an attribute and a value. The value may be a literal value, set of literal values, or an expression. The expression may contain numerical and Boolean operators and the like. Defined configurations can be nested into a hierarchy to represent inherently complex devices. In this case, an element references the set of legitimate defined configurations. The collection of elements, including expressions and nested defined configurations, are identified as the value requirements of the defined configuration. The defined configurations allow the CMDB evaluate to stored device information that can be used to identify a device configuration, which may in turn be used for operations such as verifying whether a software update is compatible with the device.

Enterprise users create defined configurations based on the devices that the manufacturer is building and shipping. The defined configuration is comparable to a "specification" for the device. For example, Company X creates a first version of device Y. During the creation of the product, enterprise users create many constructs describing device Y, including a device type, defined configurations, and the like, which enable many aspects of remote management. Device Y ships and the enterprise receives actual configuration updates for the purchased devices. The enterprise processes those updates (e.g., matches defined configurations to the device). Some time later Company X works on new versions of device Y and creates new defined configurations in the process. Once the new device ships, the cycle continues.

A further component of the defined configuration is the state. The value of the state of the device can include, for example, valid, recommended, obsolete, "known bad" and other states known by one skilled in the art. The defined configuration has a state or status that applies to all devices whose actual configuration matches the defined configuration. The configuration state of the device is on the defined configuration and "inherited" by devices whose actual configuration matches it. If an actual configuration does not match any of the defined configurations, then it is generically said to be "invalid." The state of the device impacts actions taken when a device's actual configuration changes or when the defined configuration status changes. For example, if a device's actual configuration changes from obsolete to recommended, no action is required. But if a defined configuration status changes from valid to known bad, immediate action may be required, including software updates, site visits, or other prescribed actions. If a defined configuration status changes from valid to obsolete, a less aggressive course of action could result, such as a low priority work order to "upgrade the device on the next site visit."

An actual configuration of the device is also stored in the CMDB. The actual configuration is collected from each device and can, for example, include hardware versions, software versions, environmental conditions, operational status, operational parameters, and other configuration information that can be collected from the device. The actual configurations, like defined configurations, can be simple or complex, for example, including values nested in a hierarchy.

The defined configuration is associated with a device type, such as a laptop, and the actual configuration is associated a particular device. The actual configuration, which is collected from the device, can then be compared to the defined configuration for the device type. For example, three devices are compared to a defined configuration of a laptop device type below. The defined type in this example is for laptops where the defined configuration is shown below in Table A:

TABLE A

| devicetype = LapTops | | | | |
|---|---|---|---|---|
| Configuration | IBM Laptops-T23 | | | |
| State | VALID | | | |
| Status | LOCKED | | | |
| | | Mandatory | | |
| Manufacturer | IBM | Y | | |
| RAM | >1 GB | Y | | |
| OS | Windows XP-Pro | Y | | |
| HardDisk | | Y | | |
| Seagate-M1 | | | WD-32 | |
| Mfg | Seagate | | Mfg | Western Digital |
| Model | 29 | 30 | 31 | | Model | 24 |
| FWVersion | 1.2.29 | | | |
| Software 1 | | N | | |
| Office 2003 | | | | |
| Word | 2003 | | | |
| Excel | 2003 | | | |
| Software 2 | | Y | | |
| QuestraSA | | | | |
| Version | 5.1.236 | | | |

The defined configuration includes various components that can be check against the actual configurations of the deices. The defined configuration includes the following values: the configuration is IBM Laptops-T23; the state is valid, and the status is locked. Other configuration values and types are defined. For example, a configuration type is the manufacturer and the value associated with it is IBM. The defined configuration can also include configuration sets, such as software 1 and software 2 shown above. A configuration set can include values that are grouped together based on various subsystems. The other configuration types are defined accordingly as shown in Table A.

Device actual configurations are compared to defined configurations to determine which, if any, defined configurations match the device. The meaning of the term match, as defined within this application, means that a value in the actual configuration of the device complies with an expression for an element in the defined configuration, which comparison includes, for example, operators such as less than (<), less than or equal to (<=), equal to (=), greater than or equal to (>=), and greater than (>), or other Boolean operators. The elements of a defined configuration can be tagged as elective or mandatory values. If the configuration element is mandatory, then the values of the actual configuration must match the respective defined value during the comparison process. If the configuration element is not mandatory, then the component is not required to be present in the system. But if the elective element is present, the configurations must match. When the actual configuration does not match any defined configuration, then the enterprise can be programmed to find the closest match for the device, and/or to run business logic to notify the technician or user, or to perform some other action.

Continuing with the example illustrated above, device 1 can include the following actual configuration shown below in Table B:

TABLE B

| Device 1 - Actual Configuration | | |
|---|---|---|
| Manufacturer | | IBM |
| RAM | | 2 GB |
| OS | | Windows XP-Pro |
| Hard | Mfg | Seagate |
| Disk | Model | 30 |
| | FWVersion | 1.2.29 |
| Software1 | Word | 2003 |
| | Excel | 2003 |
| Software2 | Version | 5.1.236 |

The actual configuration of device 1 matches the defined configuration in Table A. The hardware and software comply with the requirements in the defined configuration.

A second device in the example includes the actual configuration shown in Table C:

TABLE C

| Device 2 - Actual Configuration | | |
|---|---|---|
| Manufacturer | | IBM |
| RAM | | 2 GB |
| OS | | Windows XP-Pro |
| Hard | Mfg | Seagate |
| Disk | Model | 30 |
| | FWVersion | 1.2.29 |
| Software1 | Word | 2000 |
| | Excel | 2000 |
| Software2 | Version | 5.1.236 |

The software in the second device does not match all the fields in the defined configuration because the Word and Excel software applications are 2000, not 2003 as defined by the configuration in Table A. Although Word and Excel software are not mandatory, if the device includes the software, it must match the defined configuration. The mismatch may prompt the system to execute business logic to notify users, to fix, or to schedule an event to fix the unmatched values.

In a third device of the example, the actual configuration is shown in Table D below:

TABLE D

Device 3 - Actual Configuration

| Manufacturer |           | IBM            |
|--------------|-----------|----------------|
| RAM          |           | 512 MB         |
| OS           |           | Windows XP-Pro |
| Hard         | Mfg       | Maxtor         |
| Disk         | Model     | 30             |
|              | FW Version | 1.2.29        |
| Software2    | Version   | 5.1.236        |

There are two values that do not match the defined configuration in the third device—the size of the memory and the manufacturer. Since the values do not match and these values are mandatory, additional action must be taken to correct the mismatch. For example, new hardware can be installed to update the device to match the defined configuration.

The manufacturers can define and store configurations of devices that will ship to the field. Over the lifetime of a device, the device manufacturers can also assign or change the state of the device to indicate whether the device or its subsystems have values that are valid, recommended, obsolete, known bad, or the like. The defined configurations may be simple or complex. A complex configuration can include nested configurations or Boolean combinations of attributes and values as discussed above.

The actual configurations of each device are compared with the defined configurations to determine matches. If a device does not conform to the defined configuration or if the actual device configuration changes, business logic can run to provide notification, modify the device type or group, or schedule an action. The business logic can include, for example, user notification, external system notification (e.g. to schedule a site visit in a CRM system), schedule software updates, or run another user defined action.

Figure 2:
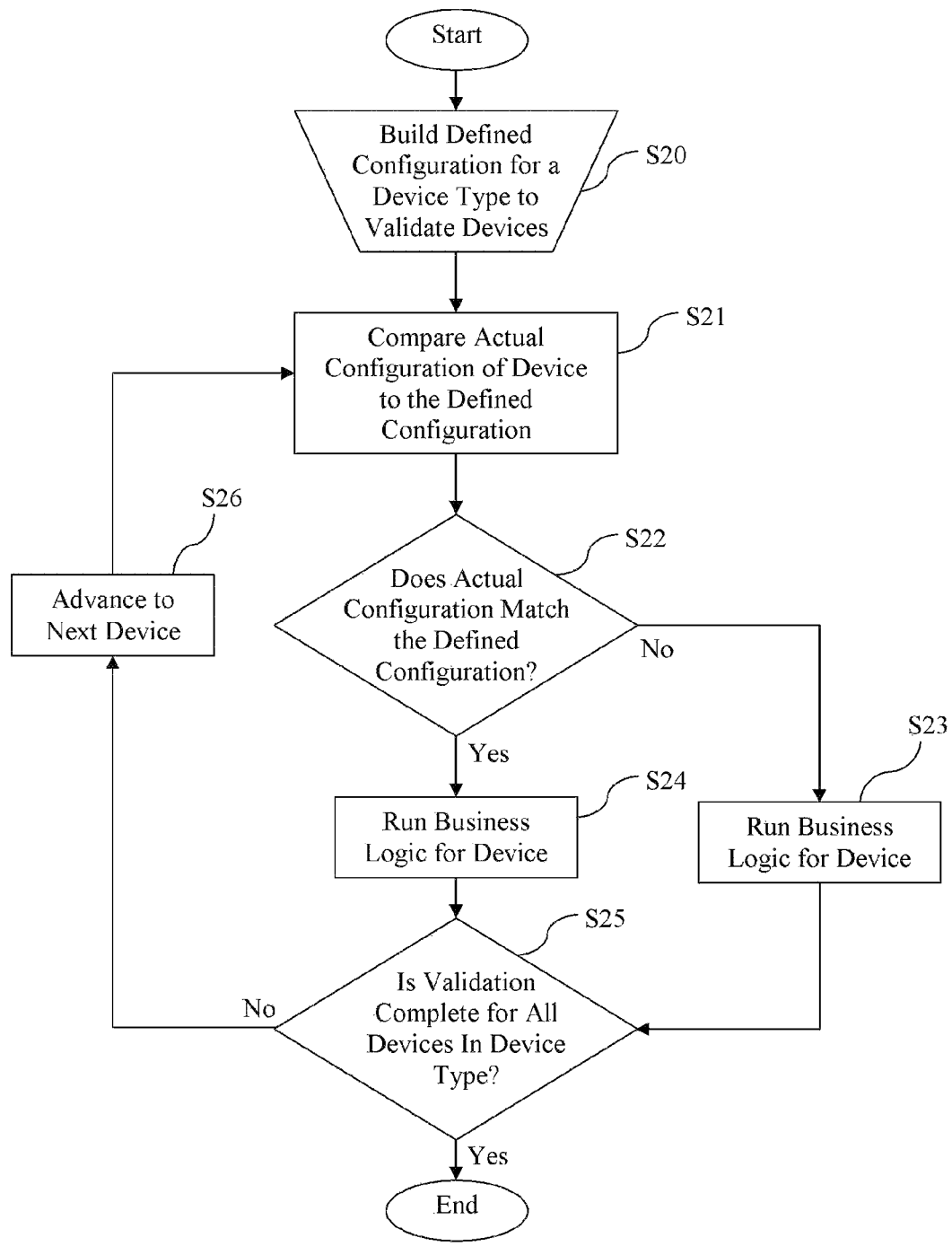
FIG. 2 is a flowchart illustrating a method of managing configurations of distributed devices in accordance an exemplary embodiment of the invention.

A method of managing configurations is illustrated in FIG. 2 in accordance with the various embodiments of the invention. The method starts in step S20 by building a defined configuration for a device type to validate the devices in the field. Step S20 can occur immediately before or much earlier than any subsequent step, for example, days, weeks, months, or even years later. A technician can build the defined configuration based on the hardware and software specification for the device. Various elements can be added to the defined configuration to match the definition of the device with the specification. If a certain component is required, the element can be tagged as mandatory. The values in the actual configuration of the device must comply with the mandatory values of the defined configuration.

Once the defined configuration is built for the device type, the system may verify each device in the device type. Generally, devices configurations are matched when the actual configuration is sent from the device to the enterprise to reduce resource utilization, such as server load. A user can also request the system to match all devices based on a previously stored configuration. The events that cause the actual configuration to be sent from the device to the enterprise include agent startup, installation of new software through the system, and manual requests from a user of the agent user interface. This event can trigger the configuration comparison and matching. In step S21, the actual configuration of the device is compared to the defined configuration. When the actual configuration does not match the defined configuration in step S22, the system can run business logic for the device in step S23 to notify users about the mismatch or to schedule an action to fix the noncompliant software or hardware in the device. The method then advances to step S25 to check if the validation process is complete for all the devices in the device type group.

When the actual configuration matches the defined configuration in step S22, the system can run business logic for the device in step S24 such as sending an update to the device, associating a state with the device, or grouping the device with other devices. The method then advances to step S25. When all the devices have been compared and matched, the process ends for the given device type.

If the validation process is not complete for all devices in the device type, the process continues to step S26 where it advances to the next device. The method then repeats the process in step S21 to compare the actual configuration of the next device in the device type against the defined configuration. The process continues until the analysis is complete for the device type or group of devices that are associated with the device type.

Figure 3:
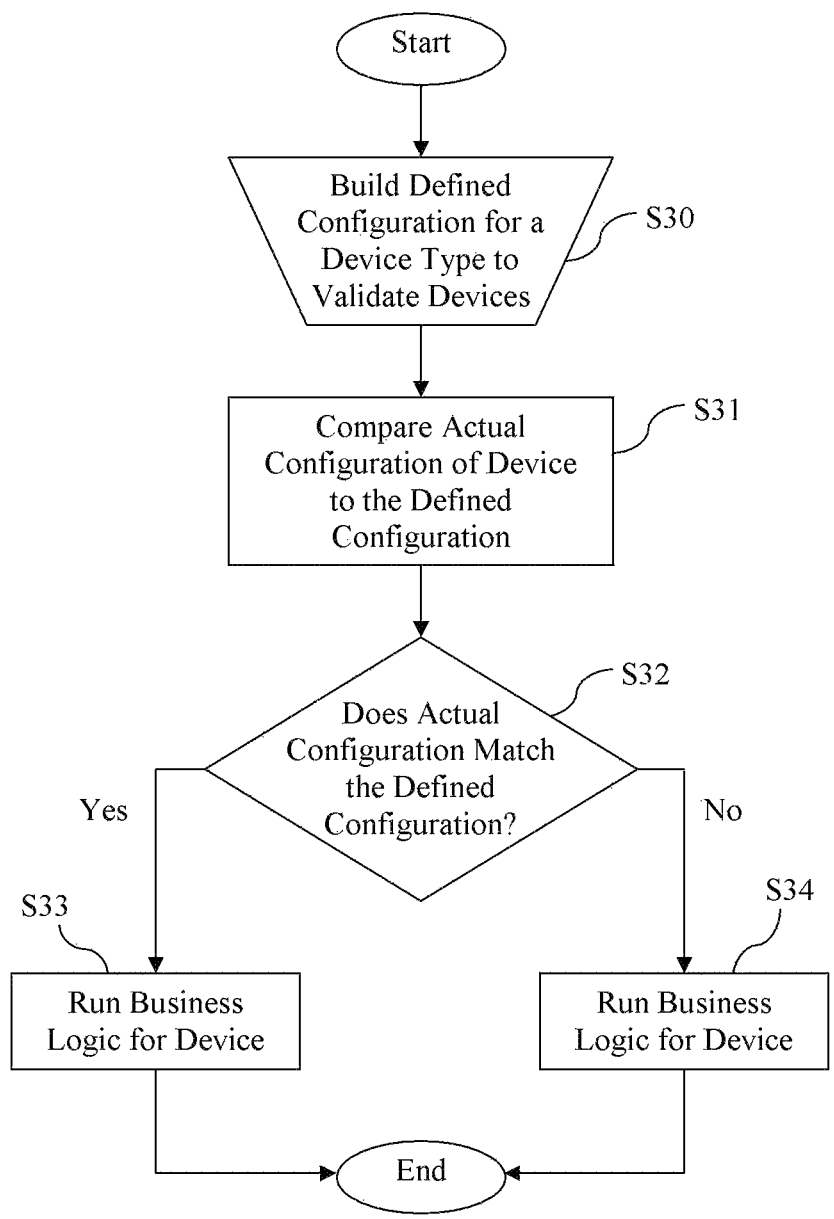
FIG. 3 is a flowchart illustrating a method of managing configurations of distributed devices in accordance with another exemplary embodiment of the invention.

Another embodiment of the invention is illustrated in FIG. 3. A method of managing configurations starts in step S30 by building a defined configuration for a device type to validate the devices in the field. The defined configuration can be built based on the device hardware and software specification. The defined configuration includes various elements that are needed to match the definition of the device with the requirements. Some elements can be tagged as mandatory if a component is required. If so, the values in the actual configuration of the device must meet or exceed the mandatory values of the defined configuration.

In step S31, the actual configuration of the device is compared against the value requirements in the defined configuration. The system then determines whether the actual configuration matches the defined configuration in step S32. If the values match, then in step S33 the system runs business logic associated with the device, such as sending a software update or configuration updates. If not, the system can run another set of business logic for the device as shown in step S34 to notify users about the mismatch or to schedule an action to fix the noncompliant software or hardware in the device. After step S33 or step S34 is complete, the process ends for the device and the data from the determined matches are stored in the database.

The system can be configured to send the software update to the device after it has been verified. In another embodiment, the system can be configured to send the update to a group of devices that have been verified at one time. After the device is verified, it can be placed in a group that corresponds to the updated devices. The groups can be based on a group type or set of group types. Device grouping is discussed in more detail below.

Optionally, the devices can be grouped together to simplify actions across multiple devices. The devices can be grouped based on certain criteria, such as geography, software application, version, extension, device type, model number, installation, division, or other device parameter. For example, the verified devices can be grouped together and the nonconforming devices can be placed in a separate group. A device can be added or removed from a given group dynamically without requiring input from any user. The movement in and out of groups can occur when an event triggers the group evaluation, such as (a) after device registration or profile updates, (b) when receiving new device operational, status, environmental data, (c) when receiving new configuration information (i.e. new versions), or (d) when alarms and/or alerts are created for a device. These groups are created automatically and may define where notifications are sent and associate other business logic to devices, such as data collection schedules, software/patch distribution schedules, and the like. The groups are arranged or created such that an administrator is no longer required review each device to verify present device conditions.

The system can collect the actual configuration of a device in the same manner as described above with respect to grouping. The data, for example, can be collected periodically, ad hoc, and on events that are likely to change the configuration, such as software and hardware upgrades. When the device information is received, business logic can be executed to send notifications or perform another action.

The devices can be associated with defined groups in the system to help organize the devices so users can locate the device easily. In addition, "bulk" operations can be performed on multiple devices including, for example, software updates or data collection, such as data readings, configuration information, file transfers, and the like. The groups can also control escalation of alert notifications. Furthermore, they can be used to control access to devices, for example, which users can view or change information regarding certain devices.

A group hierarchy also can be created if desired. The group hierarchy can include dynamically and statically defined groups, where dynamic group hierarchies start at a statically defined root group. A dynamically defined group is a group to which devices are assigned automatically. To set up a dynamic group, the user defines it by setting up criteria against which the devices are evaluated to determine their membership in the group. The statically defined group is a group whose device membership has been manually defined by an administrator. The administrator creates the group and associates devices with it. When a new device is added to the system, the administrator manually associates it with a static group. The dynamic hierarchical groups are created based on analysis of dynamic group rules and information collected directly from the device.

A dynamic group rule can be created to specify how devices will be automatically organized into groups when those devices are manually created or provide information to the enterprise. Devices can be automatically associated with groups based on a set of rules or some aspect of their profiles. As devices are added to the system or provide updated information to the enterprise, they are automatically associated with the applicable dynamic groups. A dynamic group rule causes groups to be created. The first time a device is found to match the membership criteria for a dynamic group that group is created. The static and dynamic groups have a parent group. Those at the top level have a special built-in logical parent are called a root. Groups whose parent is the root are called root groups.

Automatic groupings can be created based on device configuration data. For example, the group can be defined from the software, firmware, hardware revision information, as well as other actual configuration information. The groups are matched with defined configurations on the enterprise system 100.

The groups can also be automated based on extended and configurable registration information. The information, for example, can include device location, such as country, state, city, building, etc., or other customer information, like company name, group, responsible party, and other identifying information.

Business rules can also be applied at the device or the enterprise. The device can be grouped according to the business rule. For example, devices can be grouped based on a dynamic device property exceeding a threshold, such as a temperature, duration, pressure, or the like. If the collected information of the device meets a monitoring rule, then information can be sent to the enterprise where the system evaluates the collected information for dynamic group evaluation. The addition and removal of devices to and/or from groups manages the group-based business logic. The group-based business logic is disassociated from a group when the device is automatically disassociated from the group and group based business logic is associated to a new group when the device is automatically associated with the new group. For example, when a group has been updated, a new group can be created with the updated devices.

Automatic grouping also can be based on a device condition, such as an alert or an alarm. Alarms can be created by the monitor agent or by the enterprise system rules. When an alarm or alert is created, it triggers dynamic group rule evaluation. Alarms and alerts are defined by rules or business logic, which will be discussed below. The devices that are in a specified alert state, that is, meet a condition defined by a rule, can all be grouped together.

Business logic can also be applied to groups. For instance, if the actual configuration of a device does not match the defined configuration, then business logic can be applied. The business logic is applied to or removed from devices that enter or leave a dynamic group, respectively.

A dynamic group rule can create a hierarchy of groups, not just one flat group. A device can belong to multiple groups and subgroups in the hierarchy. The user selects which static groups to associate with the device or creates a rule specifying the device data that should be used to match the current device conditions. During the selection process, for instance, the user may choose to group the device by location, device type, and software application. The device location may be a high level group, which includes many other device types. Thus, the device type group becomes a subgroup of the device location group. Likewise, different software application groups may be found in the device type group making it a subgroup of the device type group. This relationship creates a hierarchy of groups and subgroups—the subgroups being defined within another group. Some groups may be entirely defined within a group while others may be partially defined within the group. The hierarchical groups are defined accordingly for each device.

The business logic can send notifications to users about the current or updated status of the device. The notifications can be sent to business systems or users, such as field service technicians, device operators, etc assigned to groups that are associated with a specific device in an alarm or alert condition. In one embodiment of the present invention, the notifications are defined as alarms and alerts. The alarm is a notification that is recorded and processed when a condition exists. For example, an alarm can be triggered when the actual configuration of a device does not match the defined configuration. The alarm is tracked and stored in a database. An alert is an action to be taken when the alarm condition exists. The alert, for example, can be a user notification sent by e-mail or an event notification to another business system, such as a CRM system. One alarm can generate multiple alerts, for instance, one alarm can cause an e-mail message to be sent to users and a separate notification to other business systems.

In an alternative embodiment, the notifications can escalate. After a notification has been sent to a group, if it has not been acknowledged within a defined time limit, then the notification is escalated to the next higher-level group in the hierarchy. And if the notification is not acknowledged on the higher level, then it is escalated to the next group and so forth. If the notification is acknowledged within the defined time limit, then it will not escalate to the next group. The time limit can be any defined amount of time. Typically, the time limit is defined in hours. In one example, the time limit may be set between three and five hours from the notification. The selection of a time limit is not limited to any particular range since it is based on user input.

The enterprise system 100 can include the various embodiments discussed above. The information collected from the devices is managed through the enterprise system 100 to reduce the administrative time it takes to monitor and update each device individually. The actual and defined configurations of the devices are stored in the CMDB. The values in the actual configuration are checked against the value requirements in the defined configuration to determine the configuration of the device. Business logic can be run based on the results of the comparison, for example, verifying that the software update will be compatible with the existing device and subsystems before the update is sent to the device. If the values are not compatible, business logic can be executed and a technician can update the device to make it compliant with the defined configuration. The present invention provides controlled updates to help assure that the devices will function properly after the installation is complete.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a system for communicating information between a device and an enterprise, a method for managing a configuration of the device, the method comprising:
   building a defined configuration for a device type, the defined configuration including a set of value requirements;
   comparing an actual configuration of the device to the defined configuration, the actual configuration and the defined configuration being stored in a database of the enterprise, the actual configuration having values associated with the device;
   determining, in the enterprise, a change in state of the device based on whether the values of the actual configuration match corresponding value requirements of the defined configuration;
   running business logic associated with the device based on a type of the change in state; and
   storing the actual configuration that matches the defined configuration, for subsequent use.

2. The method of claim 1, further comprising collecting information from a device information source to obtain the actual configuration of the device.

3. The method of claim 1, further comprising establishing at least one dynamic group rule based on whether the values of the actual configuration match the corresponding value requirements of the defined configuration.

4. The method of claim 1, further comprising sending a notification based on whether the values of the actual configuration match the corresponding value requirements of the defined configuration.

5. The method of claim 4, wherein the notification is an alert and sending the notification comprises sending the alert to a recipient including at least one of a user or a business system.

6. The method of claim 5, further comprising determining the recipient of the notification using group associations of a specific device in at least one of an alarm or alert condition.

7. The method of claim 1, wherein building the defined configuration for the device type includes setting at least one mandatory element in the defined configuration.

8. The method of claim 7, further comprising:
   determining if the values of the actual configuration match corresponding value requirements of the defined configuration;
   wherein the mandatory element includes a mandatory value requirement and determining if the values of the actual configuration match the corresponding value requirements of the defined configuration includes requiring a match of at least part of the actual configuration to the mandatory value requirement of the defined configuration.

9. The method of claim 7, wherein determining if the values of the actual configuration match the corresponding value requirements of the defined configuration includes indicating a match if an elective value requirement of the defined configuration is not present in the actual configuration.

10. The method of claim 1, further comprising:
    determining if the values of the actual configuration match corresponding value requirements of the defined configuration; and
    automatically associating the device with a group that reflects a result of determining if the values of the actual configuration match the corresponding value requirements of the defined configuration.

11. The method of claim 1, further comprising:
    determining if the values of the actual configuration match corresponding value requirements of the defined configuration;
    wherein determining if the values of the actual configuration match is repeated for each device in a set of devices.

12. The method of claim 11, further comprising sending an update to the device;
    wherein sending the update and running the business logic are performed after determining if the values of actual configuration match for all devices in the set of devices.

13. The method of claim 1, further comprising:
    determining if the values of the actual configuration match corresponding value requirements of the defined configuration;
    wherein determining if the values of the actual configuration match the corresponding values of the defined configuration occurs after receiving the actual configuration from the device.

14. The method of claim 1, wherein running the business logic includes sending at least one of a software and configuration update to the device.

15. The method of claim 1, further comprising:
determining if the values of the actual configuration match corresponding value requirements of the defined configuration;
wherein determining if the values of the actual configuration match the corresponding value requirements of the defined configuration includes using an expression containing at least one of a Boolean operator or a numerical comparison operator to make a comparison between the values of the actual configuration and corresponding value requirements of the defined configuration.

16. The method of claim 1, wherein building the defined configuration for the device type includes building complex defined configurations to identify the value requirements.

17. A system for managing a configuration of a device associated with a monitor agent, the system comprising:
a server configured to communicate with the monitor agent, the monitor agent being configured to collect information from the device to obtain an actual configuration of the device; and
a database storing the actual configuration of the device and a defined configuration of a device type, the device type being associated with a set of devices, the defined configuration being built for the device type and being stored in the database, the defined configuration including a set of value requirements, and the actual configuration having values associated with the device;
wherein the server is configured to compare the actual configuration to the defined configuration to determine a change in state of the device, and the server is configured to run business logic associated with the device based on a type of the change in state.

18. The system of claim 17, wherein the server is configured also to collect information from a device information source to obtain the actual configuration of the device.

19. The system of claim 17, wherein the server is configured to run the business logic if a change is determined when the actual configuration of the device is compared to the defined configuration.

20. The system of claim 19, wherein the business logic is run to enable sending a notification to at least one user including at least one of an alarm and an alert.

21. The system of claim 17, wherein:
the server is configured to assign the device a current state based on the comparison.

22. The system of claim 21, wherein the business logic is run to enforce a policy maintained for the device.

23. The system of claim 21, wherein, in a case that the current state indicates that the actual configuration of the device is valid and a prior state indicates that a prior configuration of the device is a bad configuration, the business logic is run to take immediate action.

24. The system of claim 23, wherein the immediate action comprises sending a software update to the device.

25. The system of claim 21, wherein, in a case that the current state indicates that the actual configuration of the device is obsolete and the prior state indicates that a prior configuration of the device is a valid configuration, the business logic is run to take an action that is less immediate than an action that would be taken if the current state indicates that the actual configuration of the device is valid and the prior state indicates that a prior configuration of the device is a bad configuration.

26. The system of claim 21, wherein the monitor agent is configured to detect a triggering event, to obtain the defined configuration in response to the triggering event, and to store the defined configuration in the database.

27. The system of claim 26, wherein the triggering event comprises an update or revision to the device.

28. The system of claim 21, wherein the monitor agent is configured to detect a triggering event, to obtain the actual configuration in response to the triggering event, and to store the actual configuration in the database.

29. The system of claim 28, wherein the triggering event is temporal.

30. The system of claim 21, wherein the monitor agent is configured to poll the server to enable communication between the monitor agent and the server.

31. The system of claim 17, wherein the defined configuration comprises a baseline configuration of the device, the baseline configuration being for a specific point in time and remaining unchanged within the database.

32. The system of claim 17, wherein the monitor agent comprises a plug-in module that is configured for use with the device.

33. The system of claim 17, wherein the monitor agent is configured to obtain the actual configuration also based on data obtained from one or more sources, the one or more sources comprising at least one of a database, a registry, a file system, or a data collection protocol.

34. A system comprising:
a monitor agent to collect information from a device, the information being about an actual configuration of the device; and
a computing device configured to perform operations comprising:
building a defined configuration for a device type;
storing the defined configuration in a configuration management database;
using the information to make a comparison of the actual configuration of the device to the defined configuration in order to determine a change in state of the device;
determining that an update is to be made to the device based on a type of the change in state of the device;
confirming that the update is compatible with the device based on the information about the actual configuration; and
sending the update to the device;
wherein the monitor agent and the computing device are configured to communicate over at least one communication network and are separated by network security.

35. The system of claim 34, wherein the defined configuration comprises a baseline configuration of the device, the baseline configuration not changing over time.

36. The system of claim 34, wherein the defined configuration comprises elements tagged as mandatory; and
wherein, for the comparison to indicate a match between the defined configuration and the actual configuration, the elements tagged as mandatory must have values that have a predefined relationship to corresponding values in the actual configuration.

37. The system of claim 36, wherein the defined configuration comprises elements tagged as elective, where an element tagged as elective need not be present in the actual configuration for the comparison to indicate a match.

38. The system of claim 34, wherein, for the comparison to indicate a match between the defined configuration and the actual configuration, the elements tagged as mandatory must have values that are the same as corresponding values in the actual configuration.

39. The system of claim 34, wherein the information is used to make the comparison of the actual configuration of the device to the defined configuration in order to determine if the actual configuration completely matches the defined configuration; and wherein it is determined that that an update is to be made to the device if the actual configuration does not completely match the defined configuration.

40. The system of claim 34, wherein the defined configuration comprises a nested hierarchy of multiple configurations for types of elements.

41. The system of claim 34, wherein the monitor agent is configured to poll the computing device to enable communication between the monitor agent and the computing device.

42. The system of claim 34, wherein the monitor agent is configured to collect the information from the device at specified times.

43. The system of claim 34, further comprising:

assigning a state to the device based on the comparison, a priority of the update being based on the state;

wherein a timing at which the update is sent is based on the priority.

44. Non-transitory machine-readable storage storing instructions that are executable by a computing device to perform operations that comprise:

building a defined configuration for a device type;

storing the defined configuration in a configuration management database;

receiving information about an actual configuration of a device from a monitor monitoring agent associated with the device;

using the information to make a comparison of the actual configuration of the device to the defined configuration in order to determine a change in state of the device;

determining that an update is to be made to the device based on a type of the change in state of the device;

confirming that the update is compatible with the device based on the information about the actual configuration; and sending the update to the device;

wherein the monitor agent and the computing device are configured to communicate over at least one communication network and are separated by network security.

45. The non-transitory machine-readable storage of claim 44, wherein the operations comprise establishing at least one dynamic group rule based on a result of the comparison of the actual configuration of the device to the defined configuration.

46. The non-transitory machine-readable storage of claim 44, wherein building the defined configuration for the device type includes setting at least one mandatory element in the defined configuration; and wherein the mandatory element includes a mandatory value requirement and the comparison of the actual configuration of the device to the defined configuration requires, for the actual configuration to at least partly match the defined configuration, the actual configuration to include the mandatory value requirement.

* * * * *

UNITED STATES PATENT AND TRADEMARK OFFICE
CERTIFICATE OF CORRECTION

PATENT NO. : 9,712,385 B2
APPLICATION NO. : 15/091808
DATED : July 18, 2017
INVENTOR(S) : John Louis Taylor et al.

It is certified that error appears in the above-identified patent and that said Letters Patent is hereby corrected as shown below:

On the Title Page

Item (73) ("Assignee") delete "PTC,Inc." and insert --PTC Inc.-- therefor.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*